US007082440B2

(12) United States Patent
Ogino et al.

(10) Patent No.: US 7,082,440 B2
(45) Date of Patent: Jul. 25, 2006

(54) MEDICAL IMAGE SERVICE METHOD, MEDICAL SOFTWARE SERVICE METHOD, MEDICAL IMAGE CENTRAL MANAGEMENT SERVER APPARATUS, MEDICAL SOFTWARE CENTRAL MANAGEMENT SERVER APPARATUS, MEDICAL IMAGE SERVICE SYSTEM AND MEDICAL SOFTWARE SERVICE SYSTEM

(75) Inventors: Tetsuo Ogino, Tokyo (JP); Toshihito Shiraishi, Tokyo (JP); Toshio Tsunoda, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 466 days.

(21) Appl. No.: 09/900,569

(22) Filed: Jul. 5, 2001

(65) Prior Publication Data
US 2002/0029264 A1 Mar. 7, 2002

(30) Foreign Application Priority Data

Sep. 4, 2000 (JP) ............................. 2000-266560
Mar. 14, 2001 (JP) ............................. 2001-071313

(51) Int. Cl.
*G06F 17/30* (2006.01)
*G06F 15/173* (2006.01)
*G06Q 10/00* (2006.01)
*A61B 5/00* (2006.01)

(52) U.S. Cl. .................... 707/104.1; 707/10; 707/102; 705/2; 705/3; 709/223; 600/300; 600/301

(58) Field of Classification Search .................. 707/1, 707/10, 102, 104.1; 382/141; 705/2, 3; 709/223; 715/512, 513; 369/1; 600/300, 600/301
See application file for complete search history.

(56) References Cited

U.S. PATENT DOCUMENTS

| | | | | |
|---|---|---|---|---|
| 4,835,372 A | * | 5/1989 | Gombrich et al. | 235/375 |
| 4,857,716 A | * | 8/1989 | Gombrich et al. | 235/375 |
| 5,553,609 A | * | 9/1996 | Chen et al. | 600/301 |
| 5,581,460 A | * | 12/1996 | Kotake et al. | 705/3 |
| 5,619,991 A | * | 4/1997 | Sloane | 600/300 |
| 5,734,915 A | * | 3/1998 | Roewer | 715/512 |
| 5,867,821 A | * | 2/1999 | Ballantyne et al. | 705/2 |
| 5,911,687 A | * | 6/1999 | Sato et al. | 600/300 |
| 6,272,470 B1 | * | 8/2001 | Teshima | 705/3 |
| 6,381,029 B1 | * | 4/2002 | Tipirneni | 358/1.14 |
| 6,424,996 B1 | * | 7/2002 | Killcommons et al. | 709/206 |
| 6,501,849 B1 | * | 12/2002 | Gupta et al. | 382/141 |
| 6,564,256 B1 | * | 5/2003 | Tanaka | 709/219 |
| 6,912,317 B1 | * | 6/2005 | Barnes et al. | 382/239 |

* cited by examiner

Primary Examiner—Shahid Alam
(74) Attorney, Agent, or Firm—Moonray Kojima

(57) ABSTRACT

An image processing system having a server which applies image processing to a medical image sent by a subscriber via a generally available network, such as the "internet", and sends the results of the image processing back to that subscriber or to another subscriber as instructed upon verification of the legitimacy of the instructions. In this manner, the processing load is reduced and medical images are made more readily and easily accessible.

17 Claims, 17 Drawing Sheets

| Registrant | Patient ID | Imaging Date | Apparatus ID | Image Data |
|---|---|---|---|---|
| A-hospital | A12345 | 2000-3-23 10:35 | A_MRI#2 | 1110010100... |
| A-hospital | A12345 | 2000-3-23 11:47 | A_MRI#1 | 1101001000... |
| A-hospital | A12345 | 2000-3-28 13:21 | A_CT#1 | 1111010011... |
| A-hospital | A12345 | 2000-3-28 10:38 | A_X#1 | 0111010001... |
| A-hospital | A12345 | 2000-4-11 15:38 | A_CT#1 | 1100100101... |
| B-hospital | B22716 | 2000-6-15 10:26 | B_MRI#1 | 1101101001... |
| B-hospital | B22716 | 2000-6-15 10:58 | B_MRI#1 | 0100111011... |
| B-hospital | B23857 | 2000-6-20 14:16 | B_MRI#1 | 1101101101... |
| C-hospital | C52712 | 2000-3-30 10:53 | C_MRI#1 | 1101001011... |
| C-hospital | C52712 | 2000-3-30 11:35 | C_MRI#1 | 0010110110... |
| C-hospital | C52868 | 2000-4-12 15:16 | C_MRI#1 | 1101011011... |
| C-hospital | C52887 | 2000-4-13 11:21 | C_CT#1 | 0001110111... |

FIG. 5
G1
Patient ID  A12345    Patient Name:  Tokkyo, Taro
| Delivery Specification | Imaging Date | Image Type | Apparatus ID | Site | Comment | Thumbnail |
|---|---|---|---|---|---|---|
| ☐ | 2000-3-23 10:35 | MR image | A_MRI#2 | Heart | Cardiomyopathy suspected |  |
| ☒ | 2000-3-23 11:47 | MR image | A_MRI#1 | Lung | Lung cancer suspected |  |
| ☐ | 2000-3-28 13:21 | CT image | A_CT#1 | Liver | Normal |  |
| ☐ | 2000-3-28 10:38 | X-ray image | A_X#1 | Liver | Normal |  |
| ☐ | 2000-5-16 15:16 | CT image | A_CT#1 | Pancreas | Acute pancreatitis suspected |  |
Cancel   Request Delivery

| Registrant | Patient ID | Imaging Date | Apparatus ID | Image Data | Imaging Condition |
|---|---|---|---|---|---|
| A-hospital | A123455 | 2000-3-23 10:35 | A_MRI#2 | 1110010100... | TR=2100, TE=70,... |
| A-hospital | A123455 | 2000-3-23 11:47 | A_MRI#1 | 1101001000... | TR=2400, TE=80,... |
| A-hospital | A123455 | 2000-3-28 13:21 | A_CT#1 | 1111010011... | p=3, th=1... |
| A-hospital | A123455 | 2000-3-28 10:38 | A_X#1 | 0111010001... | mAs=26,... |
| A-hospital | A123455 | 2000-4-11 15:38 | A_CT#1 | 1100100101... | p=6, th=2... |
| B-hospital | B22716 | 2000-6-15 10:26 | B_MRI#1 | 1101101001... | TR=1700, TE=60,... |
| B-hospital | B22716 | 2000-6-15 10:58 | B_MRI#1 | 0100111011... | TR=2600, TE=75,... |
| B-hospital | B23857 | 2000-6-20 14:16 | B_MRI#1 | 1101101101... | TR=2300, TE=55,... |
| C-hospital | C527712 | 2000-3-30 10:53 | C_MRI#1 | 1101001011... | TR=1500, TE=35,... |
| C-hospital | C527712 | 2000-3-30 11:35 | C_MRI#1 | 0010110110... | TR=2800, TE=70,... |
| C-hospital | C52868 | 2000-4-12 15:16 | C_MRI#1 | 1101011011... | TR=2500, TE=55,... |
| C-hospital | C52887 | 2000-4-13 11:21 | C_CT#1 | 0001110111... | p=3, th=2... |

FIG. 10
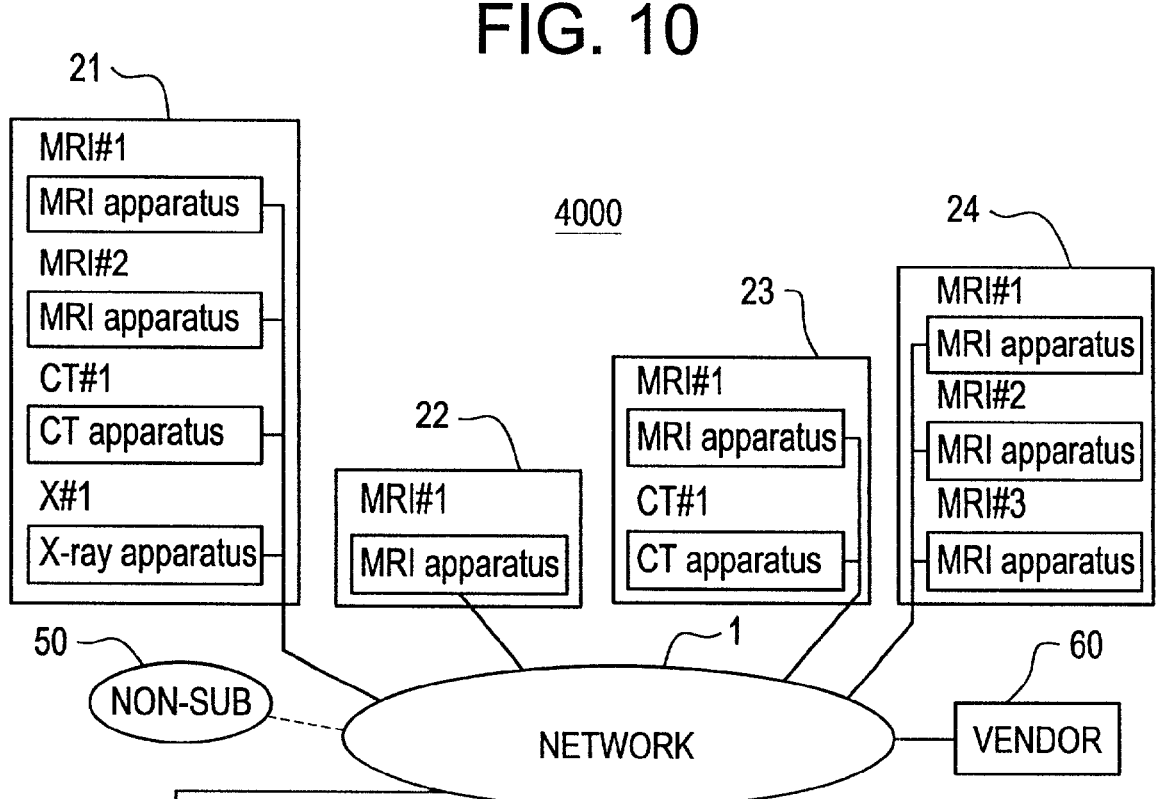
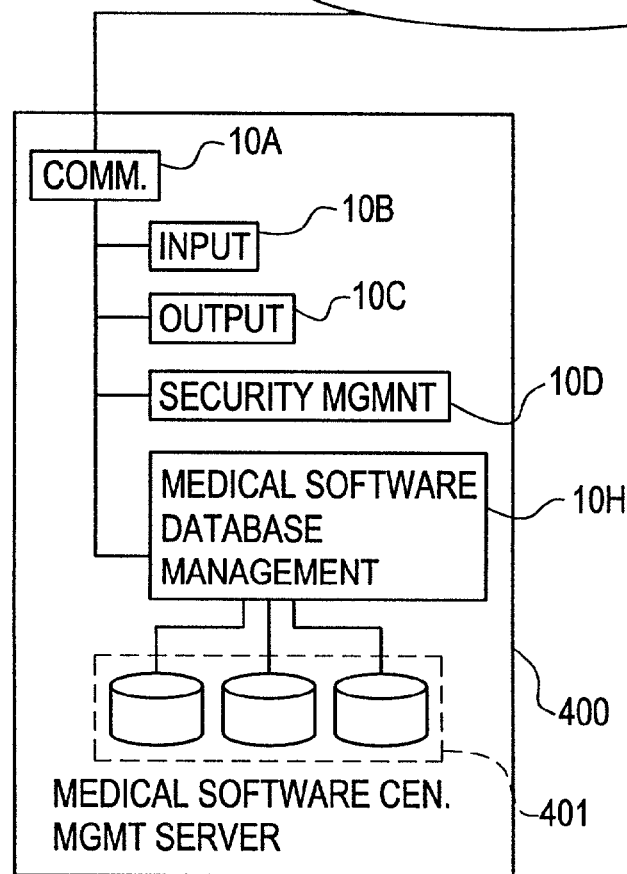

401

| Installation Site | Update Date | Apparatus ID | Medical Software ID |
|---|---|---|---|
| A-hospital | 2000-3-23  3:35 | A_MRI#1 | GEYMS_MR_SYSTEM_VER5.0 |
| A-hospital | 2000-3-23  1:47 | A_MRI#2 | GEYMS_MR_SYSTEM_VER5.0 |
| A-hospital | 2000-3-28  3:21 | A_CT#1 | GEYMS_CT_SYSTEM_VER7.3 |
| A-hospital | 2000-3-28  4:38 | A_X#1 | GEYMS_X_SYSTEM_VER3.0 |
| B-hospital | 2000-6-15  5:26 | B_MRI#1 | GEYMS_MR_SYSTEM_VER8.0 |
| C-hospital | 2000-3-30  6:53 | C_MRI#1 | GEYMS_MR_SYSTEM_VER7.0 |
| C-hospital | 2000-4-13  2:21 | C_CT#1 | GEYMS_CT_SYSTEM_VER6.0 |

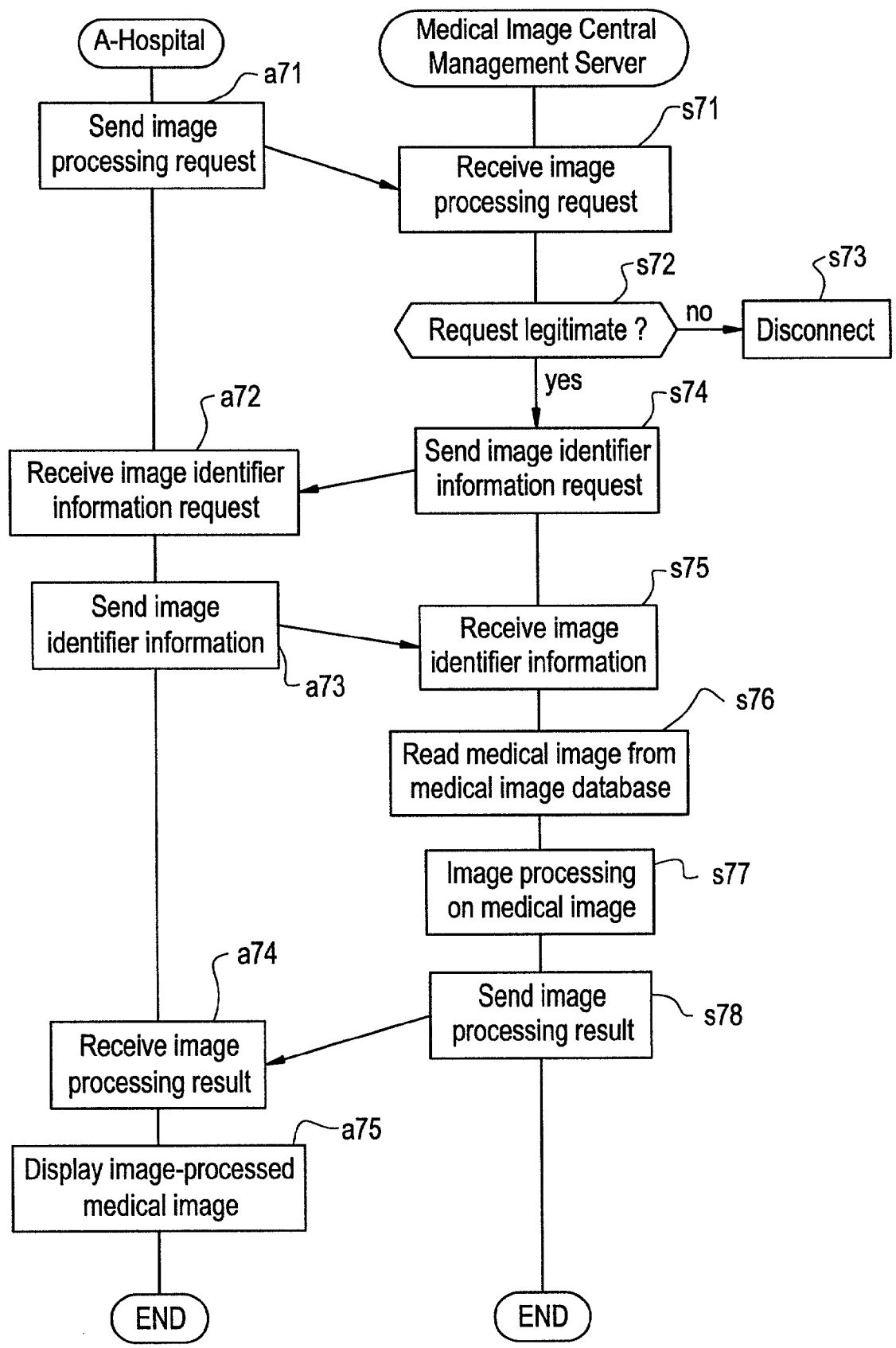

MEDICAL IMAGE SERVICE METHOD, MEDICAL SOFTWARE SERVICE METHOD, MEDICAL IMAGE CENTRAL MANAGEMENT SERVER APPARATUS, MEDICAL SOFTWARE CENTRAL MANAGEMENT SERVER APPARATUS, MEDICAL IMAGE SERVICE SYSTEM AND MEDICAL SOFTWARE SERVICE SYSTEM

BACKGROUND OF THE INVENTION

The present invention relates to a medical image service method, medical software service method, medical image central management server apparatus, medical software central management server apparatus, medical image service system and medical software service system. More particularly, the present invention relates to a medical image service method, medical software service method, medical image central management server apparatus and medical software central management server apparatus which can reduce the work of managing medical images and medical software, relative to individual management thereof, at the installation site of a medical image diagnosis apparatus, and a medical image service system and medical software service system which can reduce the work of management and image processing relative to individual management and image processing.

In general, medical images taken at a hospital are accumulated in a local storage device in the hospital for management. For example, the images are accumulated on a hard disk device attached to an MRI apparatus or a CT apparatus. So that medical images taken at one hospital can be used at another hospital, a medical information service system is known which sends the medical images from a terminal in the former hospital to a terminal in the latter hospital via a network.

In addition, a hospital installs and manages the medical software (application programs) necessary for operating its medical image diagnosis apparatuses independently of other hospitals. The medical software programs used to operate MRI apparatuses and CT apparatuses, for example, are frequently improved, so that it is necessary to install patch software to upgrade the installed medical software every time an improvement is made.

When medical images are accumulated in a local storage device as in the past, the following problems arise:

(1) An MR image or a CT image has a relatively large data size. For example, an MR image with 256×256 dots and two-byte intensity has a data size of 128 kilobytes. However, a local storage device often has a storage capacity intended only for minimum practical use in a common hospital because of restriction on cost or the like, and the device cannot perform well in a hospital which requires an especially large number of images taken or an especially long image storage period. For example, assuming that three MRI apparatuses are installed in one hospital, and each MRI apparatus takes 1,000 images (=assuming the number of patients to be 20, and the number of images taken per patient to be 50) a day, the data size will be 128 megabytes a day and will be 37.5 gigabytes a year (assuming the number of operation days to be 300), which leads to difficulty in accumulating and managing MR images over many years in the instrument having a small storage capacity.

(2) In order to use a medical information service system, it is necessary for the sender and the recipient to make a contract with each other. In other words, each party must make as many contracts as the number of partners it has, which is troublesome. Accordingly, the number of partners is limited to a small number in practice.

(3) In order to use a medical information service system, the user needs to connect the partner's address by inputting the address through a terminal. When the number of the partners is large, the user cannot remember all of their addresses. The work of searching for a partner's address therefore takes place every time the address is needed, which is troublesome. Accordingly, the number of partners is limited to a small number in practice.

Moreover, when a medical image diagnosis apparatus performs image processing on a medical image, the following problems arise:

(1) If image processing is executed simultaneously with processing for imaging of a subject, the speed of one or both of the processing operations is liable to be lowered, and the processing time is prolonged in proportion.

(2) A separate image processing program must be installed in each medical image diagnosis apparatus. In other words, only a purchaser of the image processing program can use the program.

Furthermore, when medical software for medical image diagnosis apparatuses are separately managed in individual hospitals as in the past, the following problems occur:

(1) Each time new medical software is released, the hospitals must install it separately, which is time-consuming. Moreover, the work of software version management also falls on the hospital and is not an easy task.

(2) Since medical software can be updated only after the hospital obtains it as patch software recorded on a storage medium (such as an FD or MO), the time of the actual update is delayed relative to the release date. This is especially inconvenient when new hardware is introduced (for example, a new type of RF coil is installed in an MRI apparatus).

SUMMARY OF THE INVENTION

It is therefore a first object of the present invention to provide a medical image service method and system which can alleviate the effect of restricted storage capacity in the storage of medical images, and which can deliver medical images to a multiplicity of parties via a network without need for the troublesome work of making contracts or conducting searches. It is also within this object to provide a server apparatus for this purpose.

A second object of the present invention is to provide a medical image service system which can reduce image processing load, and which can make a medical image subjected to image processing easily available.

A third object of the present invention is to provide a medical software service method and system which can reduce the work of managing medical software at the installation site of a medical image diagnosis apparatus, and which enables immediate utilization of the latest medical software at all times. It is also within this object to provide a server apparatus for this purpose.

In accordance with a first aspect, the present invention provides a medical image service method characterized in that an image-registering subscriber permitted to register medical images, an image-receiving subscriber permitted to receive medical images, and a server apparatus for centrally managing medical images are connected via a network; and said server apparatus registers medical images sent by said image-registering subscriber in a database and delivers said medical images to said image-receiving subscriber.

In the medical image service method of the first aspect, since a server apparatus registers medical images sent by an image-registering subscriber via a network in a database, the number of medical images that an image-registering subscriber can store is not restricted by its local storage capacity. Specifically, since server apparatuses are as a general practice designed for the purpose of handling enormous volumes of stored information and to have a storage medium that is enhanced in maintainability and extensibility, the restriction on the storage capacity is substantially eliminated, and a large number of medical images taken in the past can be efficiently accumulated.

Moreover, since the server apparatus delivers medical images to an image-receiving subscriber via the network, medical images can also be delivered to a multiplicity of parties without need for the troublesome work of making contracts or conducting searches.

In accordance with a second aspect, the present invention provides the medical image service method of the foregoing configuration, characterized in that said medical images are those associated with at least one of MRI (magnetic resonance imaging), X-ray CT (computed tomography), ultrasound, PET (positron emission computed tomography), digitized X-ray (digital X-ray imaging and digitization of X-ray films) and CR (computed radiography).

In the medical image service method of the second aspect, several kinds of medical images (associated with MRI, X-ray CT, ultrasound, PET, digitized X-ray and CR) can be efficiently accumulated and delivered.

In accordance with a third aspect, the present invention provides the medical image service method of the foregoing configuration, characterized in that the method comprises: transmitting the medical images compressed in data size on the network, and decompressing the transmitted data into the original data on the receiving end.

In the medical image service method of the third aspect, since the medical image is transmitted after being compressed in data size, the transmission time can be reduced.

In accordance with a fourth aspect, the present invention provides the medical image service method of the foregoing configuration, characterized in that said server apparatus checks the legitimacy of said image-registering subscriber or said image-receiving subscriber.

In the medical image service method of the fourth aspect, since the server apparatus checks the legitimacy of the image-registering subscriber or image-receiving subscriber, illegitimate image registration by a third party who is not an image-registering subscriber or illegitimate delivery to a third party who is not an image-receiving subscriber can be prevented.

In accordance with a fifth aspect, the present invention provides the medical image service method of the foregoing configuration, characterized in that said server apparatus makes a backup of the medical images registered in the database.

In the medical image service method of the fifth aspect, since the server apparatus makes a backup of medical images registered in the database, the medical images can be prevented from being lost when a failure occurs, thereby improving reliability. Moreover, since the image-registering subscribers do not need to individually make backups, the work of the image-registering subscribers can be reduced.

In accordance with a sixth aspect, the present invention provides the medical image service method of the foregoing configuration, characterized in that said image-receiving subscriber sends format information including image identifier information to a hard copy device, and said hard copy device obtains delivery of a medical image corresponding to said image identifier information from said server apparatus via said network, and makes a hard copy of the medical image.

In the medical image service method of the sixth aspect, when format information including image identifier information is sent to a hard copy device, the hard copy device obtains delivery of a medical image from the server apparatus via the network, and makes a hard copy of the medical image. Therefore, apparatuses other than the hard copy device can be released to execute other processing after a short time period.

In accordance with a seventh aspect, the present invention provides the medical image service method of the foregoing configuration, characterized in that said server apparatus sends via said network to the delivery destination of a medical image the imaging conditions for the medical image.

In the medical image service method of the seventh aspect, since the server apparatus sends via the network to the delivery destination of a medical image the imaging conditions of the medical image, imaging under the same imaging conditions as in the past can be done by a medical image diagnosis apparatus installed at the delivery destination without need for resetting.

In accordance with an eighth aspect, the present invention provides a medical software service method characterized in that a software-executing subscriber permitted to run medical software, and a server apparatus for centrally managing medical software are connected via a network; and said server apparatus registers medical software in a database and delivers said medical software to said software-executing subscriber.

In the medical software service method of the eighth aspect, since a server apparatus delivers medical software registered in a database to a software-executing subscriber via a network, the work for managing medical software at the installation site of a medical image diagnosis apparatus can be reduced, and the latest medical software can be run.

In accordance with a ninth aspect, the present invention provides a medical image central management server apparatus characterized in that the apparatus comprises: medical image registering means for, when registration of a medical image is requested by an image-registering subscriber connected via the network of the foregoing configuration, registering said medical image in a database; and medical image delivery means for, when delivery of a medical image is requested by an image-receiving subscriber connected via said network, reading the medical image from said database and delivering the medical image to said image-receiving subscriber.

The medical image central management server apparatus of the ninth aspect is suitable as a server apparatus for use in the medical image service method as described regarding the first aspect.

In accordance with a tenth aspect, the present invention provides a medical image central management server apparatus characterized in that the apparatus comprises: medical image/imaging condition registering means for, when registration of a medical image is requested by an image-registering subscriber connected via a network, registering said medical image and its imaging conditions in a database; and medical image/imaging condition delivery means for, when delivery of a medical image is requested by an image-receiving subscriber connected via said network, reading the medical image and imaging conditions from said database and delivering the medical image and imaging conditions to said image-receiving subscriber.

The medical image central management server apparatus of the tenth aspect is suitable as a server apparatus for use in the medical image service method as described regarding the seventh aspect.

In accordance with an eleventh aspect, the present invention provides a medical software central management server apparatus characterized in that the apparatus comprises: medical software registering means for registering in a database medical software for each software-executing subscriber which is connected via a network and is permitted to run medical software; and medical software delivery means for delivering said medical software (or the product of its execution) to said software-executing subscriber in response to an access by said software-executing subscriber.

The medical software central management server apparatus of the eleventh aspect is suitable as a server apparatus for use in the medical software service method as described regarding the eighth aspect.

In accordance with a twelfth aspect, the present invention provides a medical image service system characterized in that the system comprises: an image-registering subscriber permitted to register medical images via a network; an image-receiving subscriber permitted to receive medical images via the network; and a server apparatus for registering medical images sent by said image-registering subscriber in a database and delivering said medical images to said image-receiving subscriber.

The medical image service system of the twelfth aspect can suitably practice the medical image service method as described regarding the first aspect.

In accordance with a thirteenth aspect, the present invention provides a medical image service system characterized in that the system comprises: an image-sending/receiving subscriber permitted to send and receive medical images via a network; and an image processing server apparatus for applying image processing to said medical images and sending the processed medical images back to said image-sending/receiving subscriber.

In the medical image service system of the thirteenth aspect, since an image processing server apparatus applies image processing to medical images sent by an image-sending/receiving subscriber via a network, and sends the result back to the image-sending/receiving subscriber, the image-sending/receiving subscriber does not need to perform image processing.

Therefore, the work of the image-sending/receiving subscriber can be reduced and the inconvenience of lowering the speed of other processing can be avoided. Moreover, since each image-sending/receiving subscriber is freed from the need to independently purchase and install image processing programs, the subscriber can easily obtain the result of image processing.

In accordance with a fourteenth aspect, the present invention provides a medical image service system characterized in that the system comprises: an image-sending subscriber permitted to send medical images via a network; an image-receiving subscriber permitted to receive medical images via the network; and an image processing server apparatus for applying image processing to medical images sent by said image-sending subscriber and sending the processed medical images to said image-receiving subscriber.

In the medical image service system of the fourteenth aspect, since an image processing server apparatus applies image processing to medical images sent by an image-sending subscriber via a network, and sends the result to an image-receiving subscriber, medical images subjected to required image processing can be obtained without need for the image-sending subscriber or the image-receiving subscriber to perform image processing. Moreover, it is also possible for the image processing server apparatus to deliver medical images to a multiplicity of image-receiving subscribers via the network, which is efficient.

In accordance with a fifteenth aspect, the present invention provides the medical image service system of the foregoing configuration, characterized in that the system comprises two or more subscribers as at least one member among said image-sending/receiving subscriber, said image-sending subscriber and said image-receiving subscriber.

In the medical image service system of the fifteenth aspect, a plurality of image-sending/receiving subscribers or image-sending subscribers can send medical images to the image processing server apparatus. Moreover, a plurality of image-sending/receiving subscribers or image-receiving subscribers can obtain medical images subjected to image processing from the image processing server apparatus.

In accordance with a sixteenth aspect, the present invention provides the medical image service system of the foregoing configuration, characterized in that the system comprises a plurality of said image processing server apparatuses, and the processing is shared among said image processing server apparatuses.

In the medical image service system of the sixteenth aspect, the processing efficiency can be improved by sharing the processing load among the plurality of image processing server apparatuses.

In accordance with a seventeenth aspect, the present invention provides the medical image service system of the foregoing configuration, characterized in that at least one of said image-sending/receiving subscriber, said image-sending subscriber and said image-receiving subscriber specifies the type of image processing to communicate it to said image processing server apparatus.

In the medical image service system of the seventeenth aspect, the image-sending/receiving subscriber, image-sending subscriber and image-receiving subscriber can select the required image processing from among many types of image processing, and cause the image processing server apparatus to execute the selected image processing.

In accordance with an eighteenth aspect, the present invention provides the medical image service system of the foregoing configuration, characterized in that said image processing server apparatus informs said image-sending/receiving subscriber or said image-receiving subscriber of the type of image processing that was applied.

In the medical image service system of the eighteenth aspect, the image-sending/receiving subscriber or image-receiving subscriber can accurately ascertain the type of image processing applied to the medical image, thereby improving reliability.

In accordance with a nineteenth aspect, the present invention provides the medical image service system of the foregoing configuration, characterized in that, when said image processing is completed, said image processing server apparatus establishes communication with said image-sending/receiving subscriber or said image-receiving subscriber and sends the medical image subjected to the image processing to said image-sending/receiving subscriber or said image-receiving subscriber.

In the medical image service system of the nineteenth aspect, after the completion of image processing, the image processing server apparatus establishes communication with the image-sending/receiving subscriber or image-receiving subscriber and sends the medical image subjected to the image processing. The use time of the network can therefore be decreased to reduce communication costs.

In accordance with a twentieth aspect, the present invention provides the medical image service system of the foregoing configuration, characterized in that said image-sending/receiving subscriber or said image-receiving subscriber sends a request for a medical image subjected to image processing to said image processing server apparatus and receives said medical image via said network.

In the medical image service system of the twentieth aspect, since the image-sending/receiving subscriber or image-receiving subscriber sends a request for a medical image subjected to image processing to the image processing server apparatus, the need for processing by the image processing server apparatus to establish communication with the image-sending/receiving subscriber or image-receiving subscriber is eliminated.

In accordance with a twenty-first aspect, the present invention provides the medical image service system of the foregoing configuration, characterized in that said image processing server apparatus stores each medical image in at least one of its form before image processing and its form after image processing.

In the medical image service system of the twenty-first aspect, the image processing server apparatus can store a multiplicity of medical images taken in the past and/or medical images obtained by subjecting such images to image processing, and provide these images to the image-sending/receiving subscribers and image-receiving subscribers for use.

In accordance with a twenty-second aspect, the present invention provides the medical image service system of the foregoing configuration, characterized in that said image-sending/receiving subscriber or said image-receiving subscriber requests said image processing server apparatus to conduct image processing on part or all of the medical images stored in said image processing server apparatus, and receives the medical images subjected to the image processing from said image processing server apparatus.

In the medical image service system of the twenty-second aspect, since the image-sending/receiving subscriber or image-receiving subscriber requests image processing of medical images stored in the image processing server apparatus, the need for sending original medical images each time image processing is to be performed is eliminated, and the processing time can be reduced.

In accordance with a twenty-third aspect, the present invention provides the medical image service system of the foregoing configuration, characterized in that said image processing server apparatus polls said image-sending/receiving subscribers or said image-sending subscribers via said network to collect medical images before image processing.

In the medical image service system of the twenty-third aspect, since the image processing server apparatus polls the image-sending/receiving subscribers or image-sending subscribers to collect medical images before image processing, the work of the image-sending/receiving subscribers or image-sending subscribers for sending an original medical image to the image processing server apparatus can be reduced.

In accordance with a twenty-fourth aspect, the present invention provides the medical image service system of the foregoing configuration, characterized in that said medical images are those associated with at least one of MRI, X-ray CT, ultrasound, PET, digitized X-ray and CR.

In the medical image service system of the twenty-fourth aspect, several kinds of medical images (associated with MRI, X-ray CT, ultrasound, PET, digitized X-ray and CR) can be efficiently accumulated and delivered, and image processing can be applied to the several kinds of medical images.

In accordance with a twenty-fifth aspect, the present invention provides the medical image service system of the foregoing configuration, characterized in that the system transmits the medical images compressed in data size on the network, and decompresses the transmitted data into the original data on the receiving end.

In the medical image service system of the twenty-fifth aspect, since the medical images are transmitted after being compressed in data size, the transmission time can be reduced.

In accordance with a twenty-sixth aspect, the present invention provides the medical image service system of the foregoing configuration, characterized in that said server apparatus comprises security means for checking the legitimacy of said image-registering subscriber or said image-receiving subscriber.

In the medical image service system of the twenty-sixth aspect, since the server apparatus checks the legitimacy of the subscriber, illegitimate registering, illegitimate sending or illegitimate receiving of images by third parties who are not valid subscribers can be prevented.

In accordance with a twenty-seventh aspect, the present invention provides the medical image service system of the foregoing configuration, characterized in that said server apparatus comprises backup means for making a backup of the medical images registered in the database.

In the medical image service system of the twenty-seventh aspect, since the server apparatus makes a backup of medical images registered in the database, the medical images can be prevented from being lost when a failure occurs, thereby improving reliability. Moreover, since the image-registering subscribers do not need to individually make backups, the work of the image-registering subscribers can be reduced.

In accordance with a twenty-eighth aspect, the present invention provides the medical image service system of the foregoing configuration, characterized in that said image-receiving subscriber sends format information including image identifier information to a hard copy device, and said hard copy device makes a hard copy of a medical image sent by said server apparatus via said network.

In the medical image service system of the twenty-eighth aspect, when the image-receiving subscriber sends format information including image identifier information to the hard copy device, the hard copy device makes a hard copy of a medical image sent by the server apparatus via the network. Therefore, apparatuses other than the hard copy device can be released to execute other processing after a short time period.

In accordance with a twenty-ninth aspect, the present invention provides the medical image service system of the foregoing configuration, characterized in that said server apparatus sends via said network to the delivery destination of a medical image the imaging conditions for said medical image.

In the medical image service system of the twenty-ninth aspect, since the server apparatus sends via the network to the delivery destination of a medical image the imaging conditions for the medical image, imaging under the same imaging conditions as in the past can be done by a medical image diagnosis apparatus installed at the destination without need for resetting.

In accordance with a thirtieth aspect, the present invention provides a medical software service system characterized in that the system comprises: a software-executing subscriber permitted to run medical software via the network; and a server apparatus for registering medical software in a database and for delivering said medical software to said software-executing subscriber via said network.

In the medical software service system of the thirtieth aspect, the medical software service method as described regarding the eighth aspect can be suitably practiced.

According to the medical image service method, medical image central management server apparatus and medical image service system of the present invention, since medical images are centrally managed in a database on the server apparatus and required medical images are delivered via a network, the work for managing the medical images (and storage devices storing them) at the individual installation sites of medical image diagnosis apparatuses is reduced.

Moreover, according to the medical image service system of the present invention, since an image processing server apparatus applies image processing to a medical image and sends the result to a subscriber of an image processing service (the subscriber may include a provisional type that has no specific qualifications and a type that has entered into a specific contract), inconveniences experienced in running an image processing program on a medical image diagnosis apparatus (for example, reduction in processing speed, purchase and installation work) are eliminated, and every subscriber can obtain a medical image subjected to the required image processing any time.

Furthermore, according to the medical software service method, medical software central management server apparatus and medical software service system of the present invention, since medical software programs are centrally managed in a database on the server apparatus and required medical software is delivered via a network, the work for managing the medical software (and storage devices storing them) at the individual installation sites of medical image diagnosis apparatuses is reduced.

Further objects and advantages of the present invention will be apparent from the following description of the preferred embodiments of the invention as illustrated in the accompanying drawings.

BRIEF DESCRIPTION OF THE DRAWINGS

FIG. 3 is an exemplary diagram showing the registered contents in the medical image database after the registration processing of FIG. 2.

FIG. 5 is an exemplary diagram showing a screen for specifying a delivery-requested image.

FIG. 8 is an exemplary diagram showing the registered contents in the medical image database after the registration processing of FIG. 7.

FIG. 10 is a block diagram showing a medical software service system in accordance with a fourth embodiment.

FIG. 18 is a flow chart showing processing for applying image processing to a medical image specified by an image-sending/receiving subscriber and sending the processed image to the image-sending/receiving subscriber by an image processing server apparatus.

DETAILED DESCRIPTION OF THE INVENTION

The present invention will now be described in detail with reference to embodiments shown in the accompanying drawings.

FIRST EMBODIMENT

Figure 1:
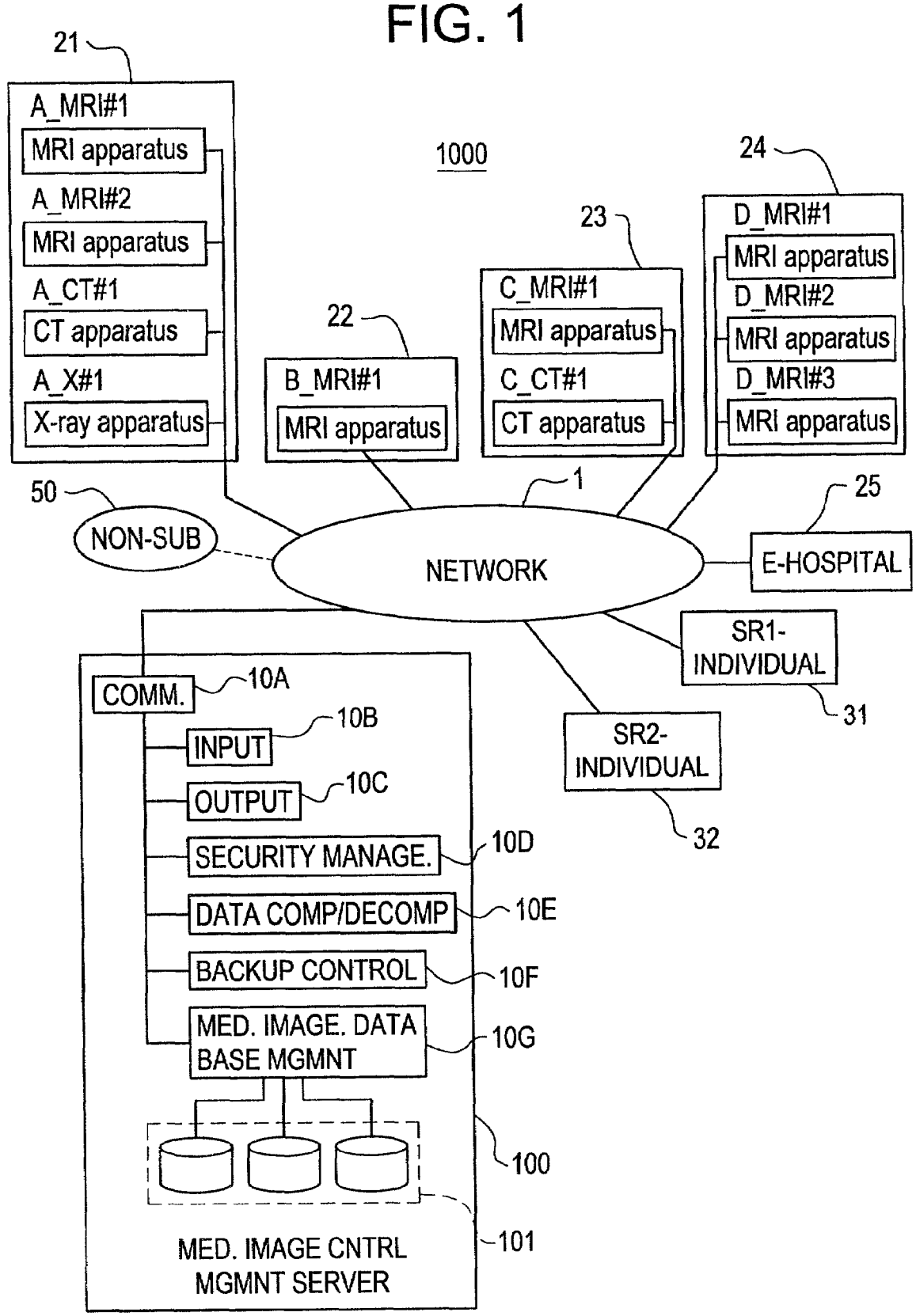
FIG. 1 is a block diagram showing a medical image service system in accordance with a first embodiment.

FIG. 1 is a block diagram showing a medical image service system 1000 in accordance with a first embodiment of the present invention.

The medical image service system 1000 comprises a network 1 such as the Internet, a LAN (local aria network) or a WAN (wide aria network), an A-hospital 21, B-hospital 22, C-hospital 23, D-hospital 24, E-hospital 25, and an SR1-individual 31 and SR2-individual 32, and a medical image central management server apparatus 100, all connected to the network 1. The communication medium for the network 1 may be wired, wireless or a combination thereof.

When the network 1 is the Internet, a non-subscriber 50 is also connected to the network 1. The non-subscriber 50 is a terminal that has not concluded a contract to use the medical image central management server apparatus 100.

In addition, it is preferred to use an SSL (secure socket layer protocol) or the like in the interest of security.

In the A-hospital 21, MRI apparatuses (A_MRI#1, A_MRI#2), a CT apparatus (A_CT#1) and an X-ray imaging apparatus (A_X#1) are installed.

In the B-hospital 22, an MRI apparatus (B_MRI#1) is installed.

In the C-hospital 23, an MRI apparatus (C_MRI#1) and a CT apparatus (C_CT#1) are installed.

In the D-hospital 24, MRI apparatuses (D_MRI#1, D_MRI#2, D_MRI#3) are installed.

Moreover, at least one of ultrasound diagnosis, PET and CR apparatuses may be installed instead of, or in addition to, the aforementioned apparatuses in any hospital.

The medical image central management server apparatus 100 comprises a communication section 10A, an input section 10B, an output section 10C, a security management section 10D, a data compression/decompression section 10E, a backup control section 10F, a medical image database management section 10G and a medical image database 101, and operates under the control of a medical image central management program. The storage medium for the medical image database 101 is a mass storage hard disk, for example.

The A-hospital 21 and B-hospital 22 have entered into contracts to register as image-registering subscribers and image-receiving subscribers of the medical image central management server apparatus 100. They act as image-registering subscribers and image-receiving subscribers by running on their terminals a registering/receiving subscriber program. This program is recorded on a storage medium (such as a CD-ROM, FD) and delivered by a manager of the medical image central management server apparatus 100, or is delivered via the network 1. Thus, the A-hospital 21 and B-hospital 22 are permitted to register and receive medical images via the network 1. It should be noted that by the symbol "/" is meant "and" ($\alpha/\beta$ means $\alpha$ and $\beta$).

The C-hospital 23 has entered into a contract to register as an image-registering subscriber of the medical image central management server apparatus 100. It acts as image-registering subscriber by running on its terminal an image-registering subscriber program. This program is recorded on a storage medium and delivered by the manager of the medical image central management server apparatus 100, or is delivered via the network 1. Thus, the C-hospital 23 is permitted to register medical images via the network 1.

The D-hospital 24, E-hospital 25, SR1-individual 31 and SR2-individual 32 have entered into contracts to register as image-receiving subscribers of the medical image central management server apparatus 100. They act as image-receiving subscribers by running on their terminals an image-receiving subscriber program. This program is recorded on a storage medium and delivered by the manager of the medical image central management server apparatus 100, or is delivered via the network 1. Thus, the D-hospital 24, E-hospital 25, SR1-individual 31 and SR2-individual 32 are permitted to receive medical images via the network 1.

The manager of the medical image central management server apparatus 100 concludes separate contracts with the individual image-registering subscribers and image-receiving subscribers, by which the image-registering subscribers are permitted to register medical images they own, and the image-receiving subscribers are permitted to obtain delivery of medical images on request. As a result of these contracts, the subscribers do not (have no need to) conclude contracts with one another. The medical image central management server apparatus 100 performs database registration of medical images owned by the image-registering subscribers via the network 1, and transfers medical images via the network 1 in response to delivery requests from the image-receiving subscribers. The server apparatus 100 also performs security management.

The manager of the medical image central management server apparatus 100 keeps subscriber information. The creation/updating of the subscriber information is performed as follows:

(1) A new subscriber makes a contract with the manager, and receives a storage medium containing a program corresponding to the type of contract. Alternatively, the new subscriber downloads the program via the network 1.

(2) When the new subscriber installs the program and runs the program the first time, the program automatically accesses the medical image central management server apparatus 100 via the network 1 and requests it to update the subscriber information. The medical image central management server apparatus 100 then adds the new subscriber to the subscriber information.

(3) When a subscriber cancels its contract, the medical image central management server apparatus 100 deletes the subscriber from the subscriber information.

The manager receives a subscription fee upon making a contract. The manager also receives a management fee regularly or irregularly for services such as maintenance and update of the subscriber information. Furthermore, the manager markets the aforementioned programs. In addition, the manager receives a registration fee from each image-registering subscriber that is proportional to the storage capacity used to register the subscriber's medical images. (A storage capacity that varies with the registration fee paid can be pre-allocated and the image-registering subscriber be informed of the allocated capacity and the capacity in use, or a registration fee can be billed depending on the storage capacity in use.) Further, the manager receives a delivery fee from the image-receiving subscriber depending on the number of medical image deliveries.

Figure 2:
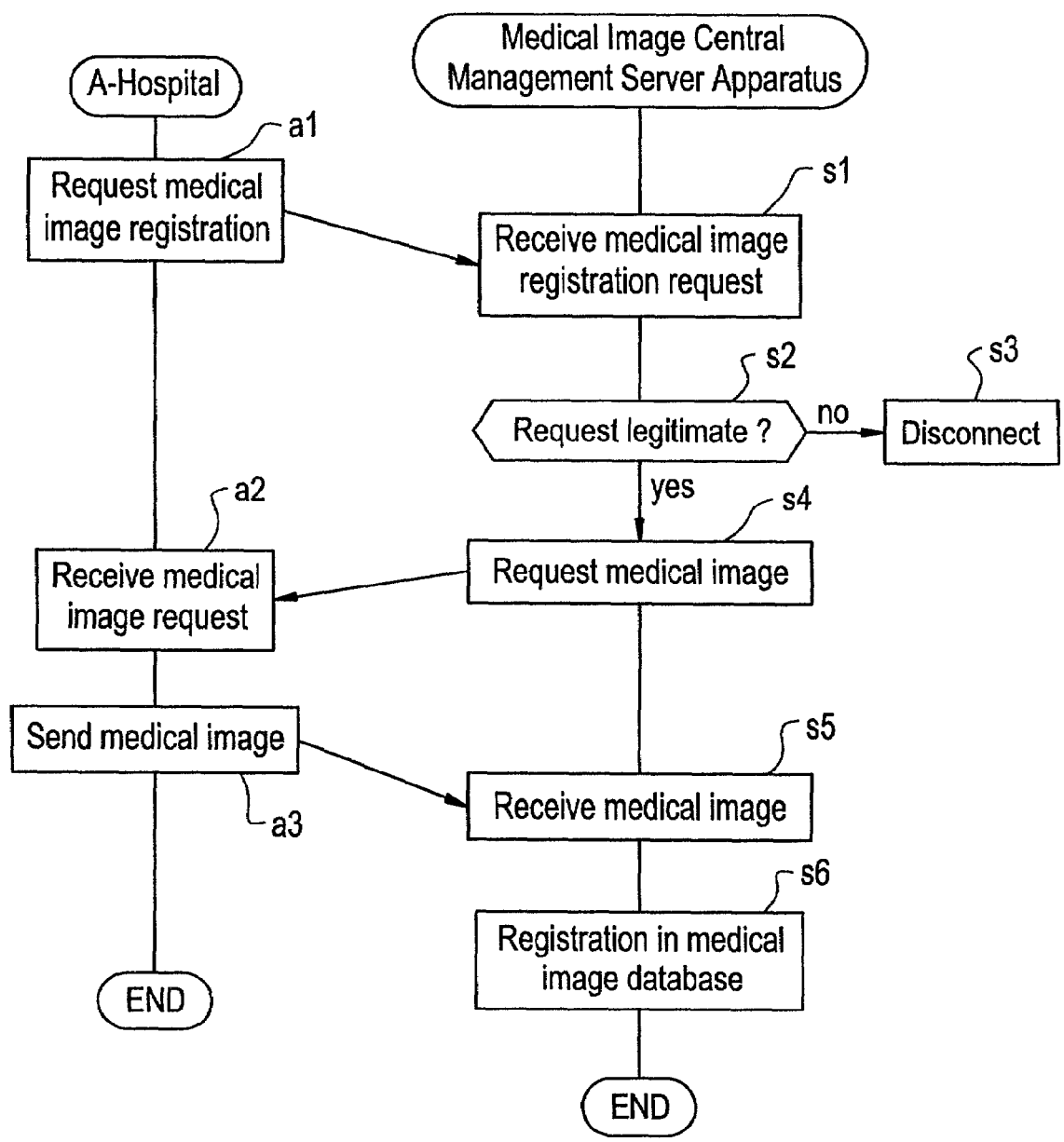
FIG. 2 is a flow chart showing medical image registration processing on a medical image database in a medical image central management server apparatus.

FIG. 2 is a flow chart showing processing for registering a medical image in the medical image database 101 in the medical image central management server apparatus 100 by an image-registering subscriber. The flow on the left is for the image-registering subscriber (assuming the image-registering subscriber to be the A-hospital 21). The flow on the right is for the medical image central management server apparatus 100.

In Step a1, the A-hospital 21 sends a request for registration of a medical image (any one of MRI, CT, X-ray images) to the medical image central management server apparatus 100 via the network 1. The medical image may be a clinical image for diagnosis on a patient, or a sample image for medical education.

In Step s1, the medical image central management server apparatus 100 receives the medical image registration request.

In Step s2, the security management section 10D of the medical image central management server apparatus 100 checks the legitimacy of the medical image registration request using an authentication technique etc., and if it is illegitimate, the process goes to Step s3; otherwise to Step s4. The check of the legitimacy uses a known legitimacy check method for communication line connection, such as a check on a network address or a telephone number, a check on a password, or a check on an ID card. Moreover, a charge billing screen (not shown) is displayed on the terminal of the A-hospital 21 to bill a connect charge, and if an operator at the A-hospital 21 performs an operation on the charge billing screen for making payment via a direct deposit from a bank account, via a credit card or a payment agency service, the request is regarded as legitimate; otherwise as illegitimate.

In Step s3, the communication line is disconnected.

In Step s4, the medical image central management server apparatus 100 sends a request for the medical image to the A-hospital 21 via the network 1.

In Step a2, the A-hospital receives the medical image request.

In Step a3, the A-hospital sends the medical image (including image identifier information) to be registered to the medical image central management server apparatus 100 via the network 1. The image identifier information may be an image ID, or combined information of a patient ID, an imaging date, an apparatus ID of a medical image diagnosis apparatus or the like. At this time, data obtained by compressing the data size of the medical image by a reversible method of compression may be sent to reduce the data transmission time. The method of compression is, for example, reversible JPEG (Joint Photographic Experts Group) compression. Moreover, the latest registered image may be temporarily stored on a local storage device (such as a hard disk or memory) as a precaution against a sudden failure of the network 1 or medical image central management server apparatus 100.

In Step s5, the medical image central management server apparatus 100 receives the medical image. If the medical image data is compressed, the data is decompressed into the original data at the data compression/decompression section 10E.

In Step s6, the medical image database management section 10G in the medical image central management server apparatus 100 registers the medical image in the medical image database 101.

The registration processing in the medical image database 101 is then terminated.

FIG. 3 is an exemplary diagram showing the registered contents in the medical image database 101 after the registration processing of FIG. 2.

In the column designated "Registrant", the A-hospital, B-hospital, C-hospital, . . . are registered, for example, as the registrants of medical images. The registrant may be received at Step a5 in FIG. 2, or may be identified based on the apparatus ID of the medical image diagnosis apparatus or the like.

In the column designated "Patient ID", A12345, B22716, B23857, . . . are registered, for example, as the patient IDs.

In the column designated "Imaging Date", 3-23-2000 10:35, 3-23-2000 11:47, 3-28-2000 13:21, . . . are registered, for example, as the imaging dates of the medical images.

In the column designated "Apparatus ID", A_MRI#2, A_MRI#1, A_CT#1, . . . are registered, for example, as the apparatus IDs of the medical image diagnosis apparatuses.

In the column designated "Image Data", 1110010100, 1101001000, 1111010011, . . . are registered, for example, as the image data of the medical images.

It should be noted that the registered contents in the medical image database 101 undergo backup upon update or regularly by the control from the backup control section 10F.

Figure 4:
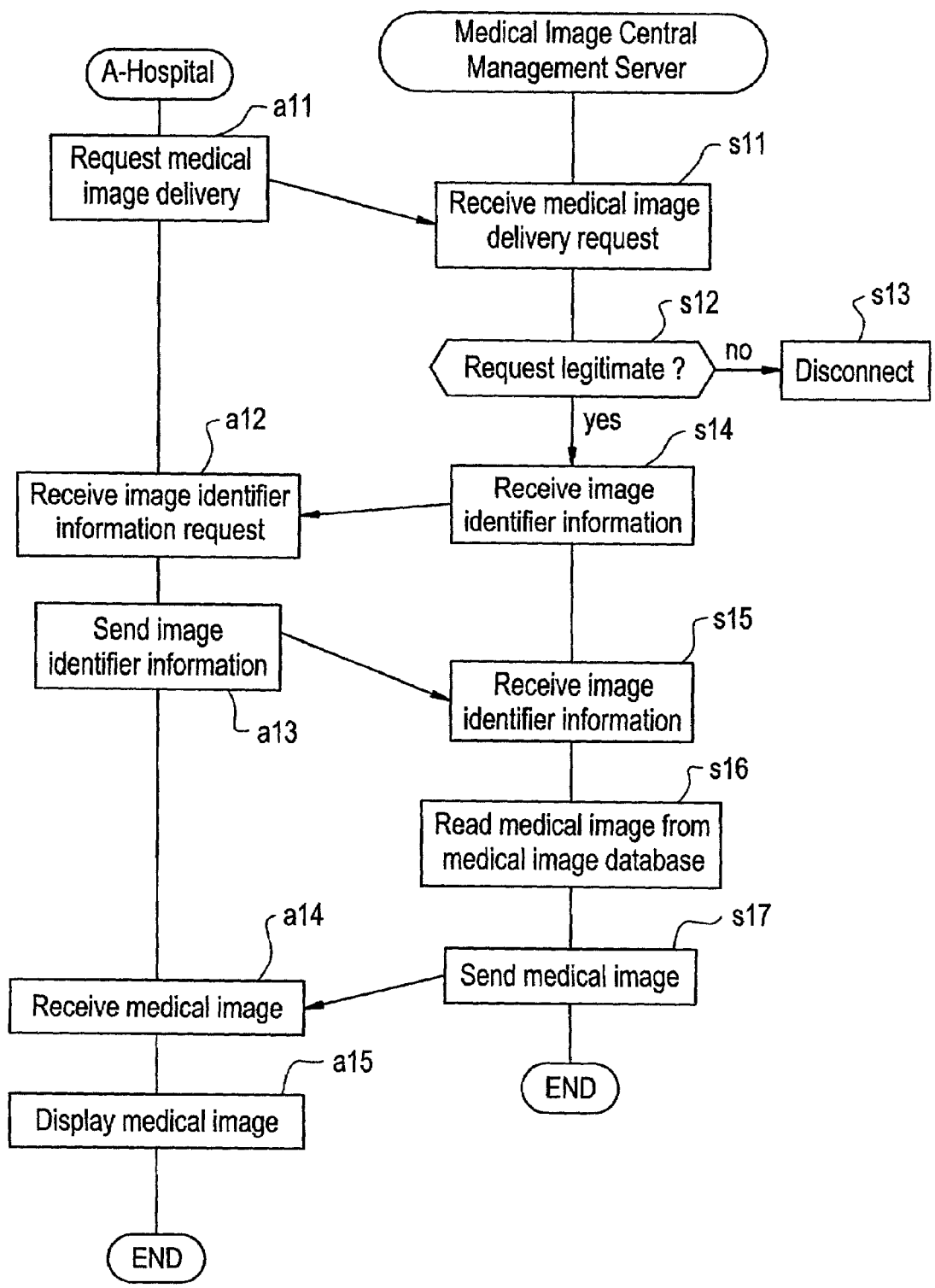
FIG. 4 is a flow chart showing processing for delivery of medical images from the medical image central management server apparatus.

FIG. 4 is a flow chart showing processing for delivering a medical image from the medical image central management server apparatus 100. The flow on the left is for the image-receiving subscriber (assuming the image-receiving subscriber to be the A-hospital 21). The flow on the right is for the medical image central management server apparatus 100.

In Step a11, the A-hospital sends a request for delivery of a medical image to the medical image central management server apparatus 100 via the network 1.

In Step s11, the medical image central management server apparatus 100 receives the medical image delivery request.

In Step s12, the security management section 10D in the medical image central management server apparatus 100 checks the legitimacy of the medical image delivery request, and if the request is illegitimate, the process goes to Step s13; otherwise to Step s14.

In Step s13, the communication line is disconnected.

In Step s14, the medical image central management server apparatus 100 sends a request for image identifier information to the A-hospital 21 via the network 1.

In Step a12, the A-hospital 21 receives the image identifier information request.

In Step a13, the A-hospital 21 sends image identifier information to the medical image central management server apparatus 100 via the network 1.

In Step s15, the medical image central management server apparatus 100 receives the image identifier information.

In Step s16, the medical image database management section 10G in the medical image central management server apparatus 100 reads the medical image corresponding to the image identifier information from the medical image database 101.

In Step s17, the medical image central management server apparatus 100 sends the read-out medical image to the A-hospital 21 via the network 1. The data compression/decompression section 10E may send data obtained by compressing the data size of the medical image by a reversible method of compression.

In Step a14, the A-hospital 21 receives the medical image. If the medical image data is compressed, the data is decompressed into the original data.

In Step a15, the A-hospital 21 displays the received medical image on a screen. The latest displayed image may be temporarily stored on a local storage device as a precaution against a sudden failure of the network 1 or medical image central management server apparatus 100.

The medical image delivery processing is then terminated.

FIG. 5 is an exemplary diagram showing a delivery-requested image specifying screen G1 for specifying an image requested for delivery on a terminal at the A-hospital 21. The screen is displayed by, for example, inputting a patient ID and then clicking "Display List". The data used for displaying the imaging date, image type, apparatus ID, site, comment and thumbnail may be stored on a local hard disk in the A-hospital 21, or may be received from the medical image central management server apparatus 100 via the network 1 (in the latter case, the necessary data is previously stored in the medical image database 101). Since the thumbnail can be displayed in small data size, a multiplicity of thumbnails can be stored even in a hard disk of a small capacity.

The operator selects a delivery specification frame corresponding to the medical image whose delivery is desired, for example, an MR image having an imaging date of [3-23-2000 11:47], by a mouse etc., and then selects "Request Delivery". Then, a delivery request is sent (see Step a11 in FIG. 4), subsequently image identifier information corresponding to the specified image is sent (see Step a13 in FIG. 14), and a medical image delivered from the medical image central management server apparatus 100 via the network 1 can be received (see Step a14 in FIG. 4). If "Cancel" is selected before selecting "Request Delivery", the image specification is canceled.

According to the medical image service system 1000 of the first embodiment, since medical images obtained by the hospitals are registered in the medical image database 101 in the medical image central management server apparatus 100 and are centrally managed, the problem of restricted storage capacity is substantially eliminated, and a large number of medical images taken in the past can be efficiently accumulated.

Moreover, since medical images can be shared among the hospitals, the system is capable of dealing with, for example, cases in which a physician observes a medical image at a location other than the installation site of an MRI apparatus; in which a patient transfers to another hospital and medical images for the patient are provided to a physician at the new hospital; and in which an individual patient desires to view his/her medical images on a personal computer terminal or the like (however, the individual patient must directly or indirectly enter into a contract with the manager of the medical image central management server apparatus 100).

Furthermore, since a backup of the medical images is made by the medical image central management server apparatus 100, the work of the individual hospitals separately preparing backups is eliminated.

SECOND EMBODIMENT

Figure 6:
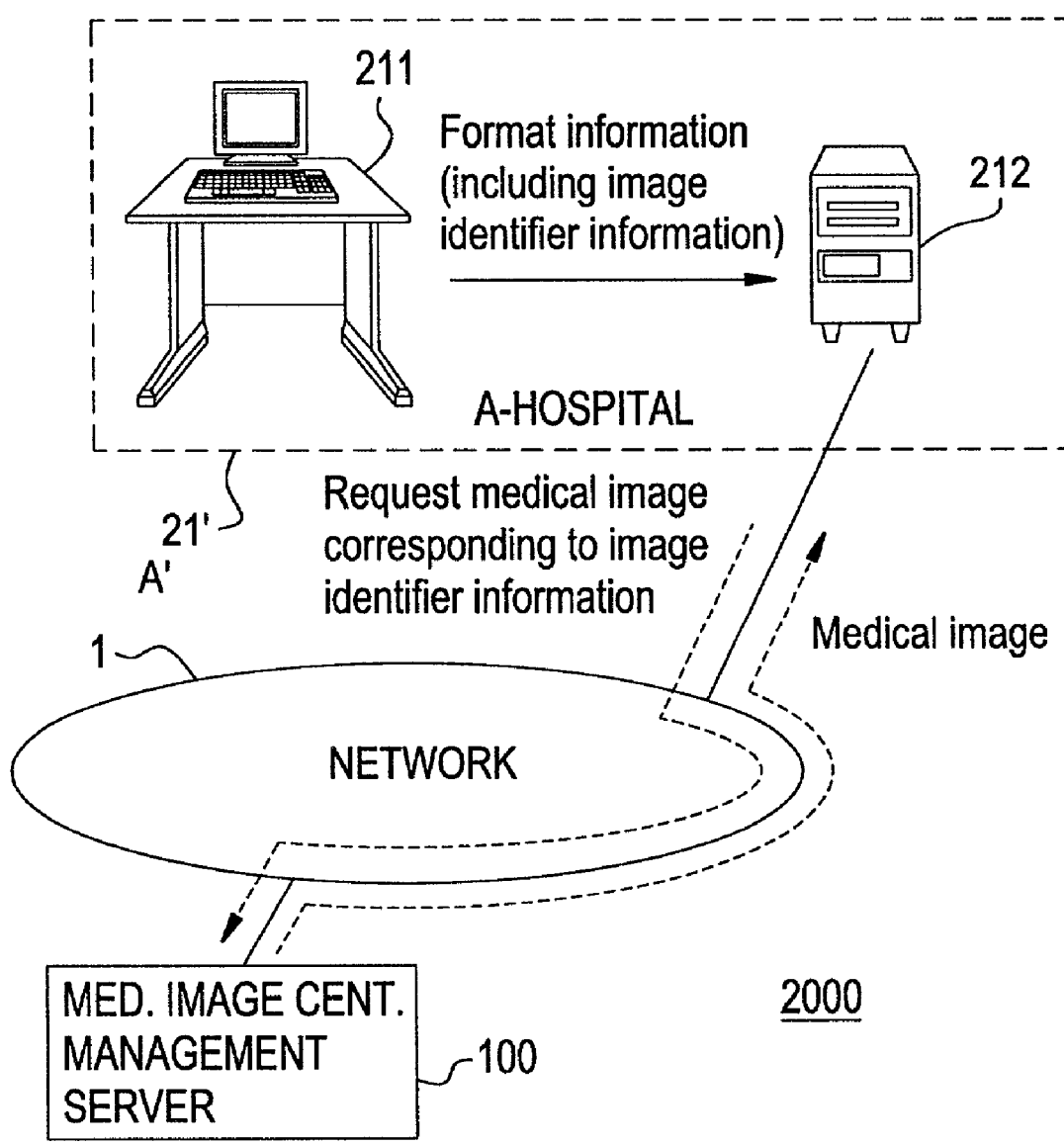
FIG. 6 is a block diagram showing a medical image service system in accordance with a second embodiment.

FIG. 6 is a block diagram showing a medical image service system 2000 in accordance with a second embodiment.

A terminal 211 of an image-receiving subscriber (assumed to be an A-hospital 21) sends to its associated hard copy device 212 format information defining the frame position, image size and the like of a medical image to be printed on a film. It should be noted that the format information contains image identifier information for identifying the medical image for each frame. The hard copy device 212 is, for example, a multi-format camera or a laser imager.

Upon receiving the format information, the hard copy device 212 sends a request for delivery of the medical image corresponding to the image identifier information to the medical image central management server apparatus 100 via the network, and receives the medical image. Then the hard copy device 212 prints the medical image in the area corresponding to the frame position and the image size.

According to the medical image service system 2000 of the second embodiment, when the terminal 211 sends format information to the hard copy device 212, the device 212 obtains delivery of a medical image from the medical image central management server apparatus 100 via the network 1 and prints the medical image on a film. The terminal 211 can therefore be released from the processing for the hard-copy production and return to other processing after a short time period.

THIRD EMBODIMENT

Figure 7:
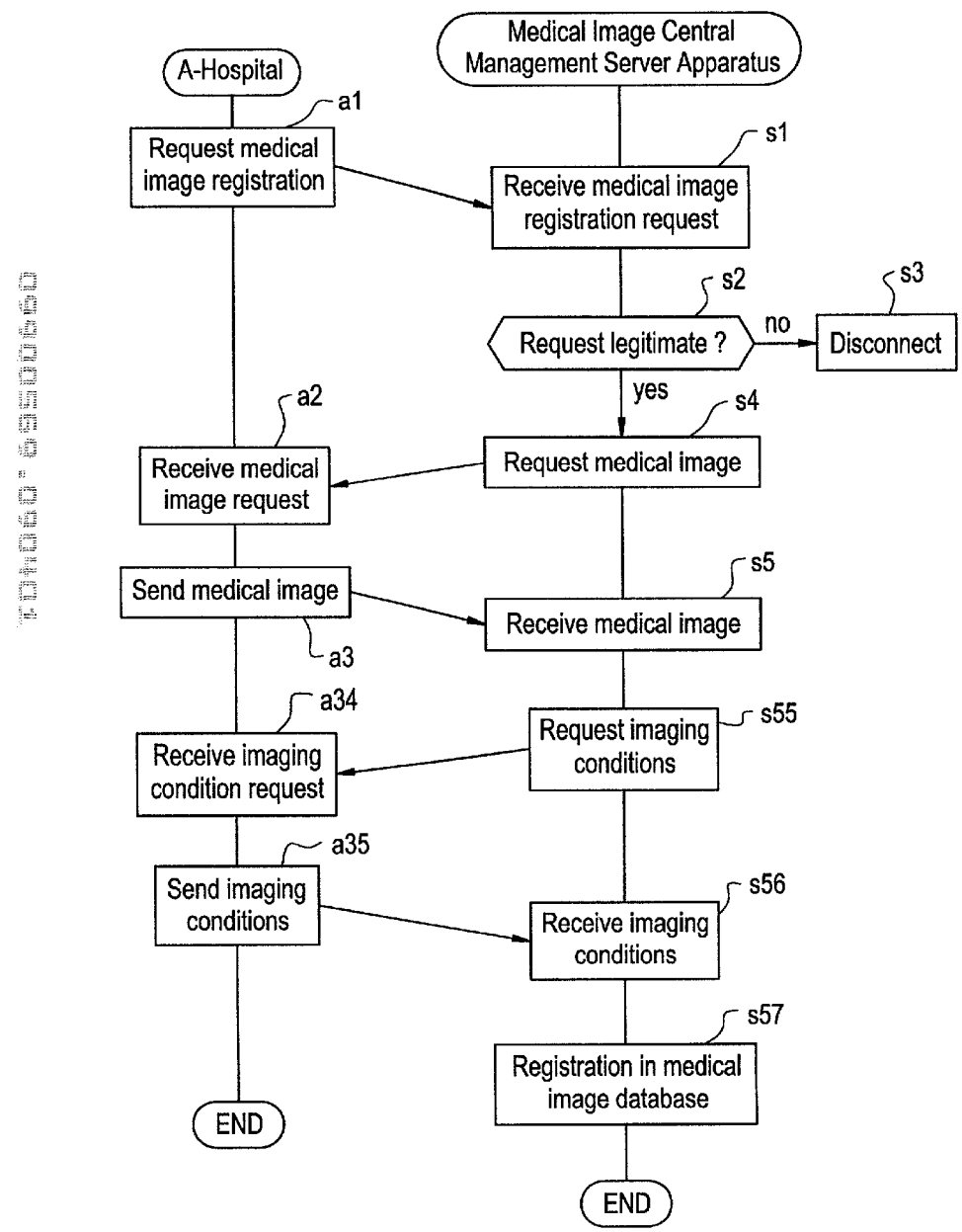
FIG. 7 is a flow chart showing medical image registration processing in the medical image service system in accordance with a third embodiment.

FIG. 7 is a flow chart showing processing for registering a medical image in a medical image service system in accordance with a third embodiment. The flow on the left is for the image-registering subscriber. The flow on the right is for the medical image central management server apparatus 200 (corresponding to 100 in FIG. 1).

Steps a1–a3 are the same as the processing described with reference to FIG. 2, and therefore the explanation thereof will be omitted.

Steps s1–s5 are the same as the processing described with reference to FIG. 2, and therefore the explanation thereof will be omitted.

In Step s55, the medical image central management server apparatus 200 sends a request for the imaging conditions of the medical image registered in the medical image database 101 to the A-hospital 21 via the network 1.

In Step a34, the A-hospital 21 receives the imaging condition request.

In Step a35, the A-hospital 21 sends the imaging conditions to the medical image central management server apparatus 200 via the network 1.

In Step s56, the medical image central management server apparatus 200 receives the imaging conditions.

In Step s57, the medical image database management section 10G (see FIG. 1) in the medical image central management server apparatus 200 registers the imaging conditions in a medical image database 201 (corresponding to 101 in FIG. 1).

The registration processing on the medical image database 201 is then completed.

FIG. 8 is an exemplary diagram showing the registered contents in the medical image database 201 after the registration processing of FIG. 7.

The registered contents in the columns designated "Registrant", "Patient ID", "Imaging Date", "Apparatus ID" and "Image Data" are the same as those of the medical image database 101 shown in FIG. 2.

In the column designated "Imaging Condition", imaging conditions of the medical images are registered. For example, for an MR image, TR (repetition time)=2400, TE (echo time)=80 and the like are registered; for a CT image, p (helical pitch)=3 and the like are registered; and for an X-ray image, mAs (tube current)=26 and the like are registered.

Figure 9:
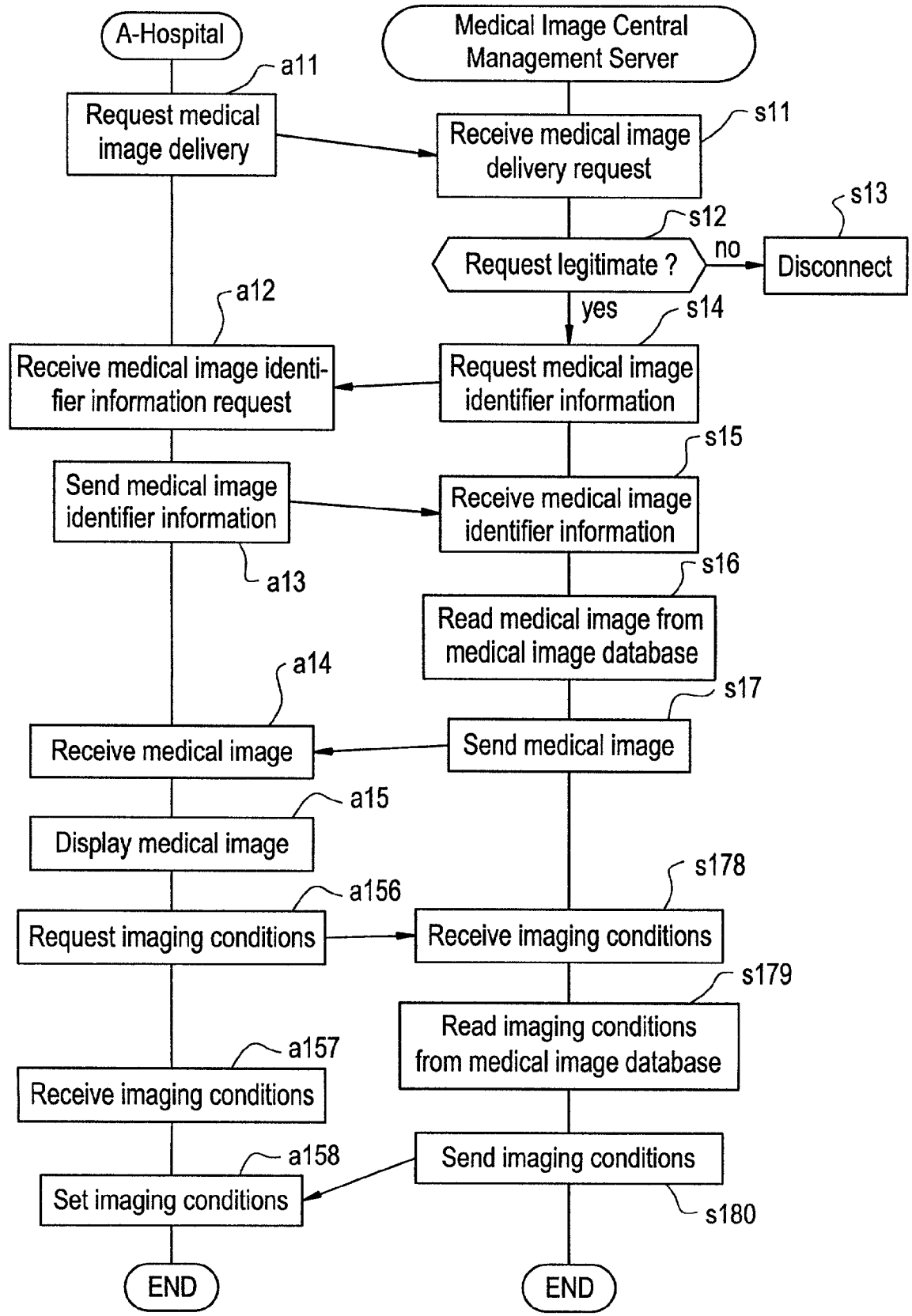
FIG. 9 is a flow chart showing processing for delivery of medical images and imaging conditions from the medical image central management server apparatus.

FIG. 9 is a flow chart showing processing for delivering a medical image and imaging conditions from the medical image central management server apparatus 200 to an image-receiving subscriber. The flow on the left is for the image-receiving subscriber. The flow on the right is for the medical image central management server apparatus 200.

The processing in Steps a11–a15 are the same as those described with reference to FIG. 4, and therefore the explanation thereof will be omitted.

Steps s11–s17 are the same as the processing described with reference to FIG. 4, and therefore the explanation thereof will be omitted.

In Step s156, the A-hospital 21 sends a request for imaging conditions to the medical image central management server apparatus 200 via the network.

In Step s178, the medical image central management server apparatus 200 receives the imaging condition request.

In Step s179, the medical image database management section 10G in the medical image central management server apparatus 200 reads from the medical image database 201 imaging conditions corresponding to the medical image delivered to the A-hospital 21.

In Step s180, the medical image central management server apparatus 200 sends the imaging conditions to the A-hospital 21 via the network 1.

In Step s157, the A-hospital receives the imaging conditions.

In Step s158, the received imaging conditions are set in a medical image diagnosis apparatus. For example, if TR=2400 and TE=80 are sent as imaging conditions for an MR image, these conditions are set in an MRI apparatus. Thus, the imaging conditions do not need to be reset, and a subject can be scanned under the same imaging conditions as in the past.

The processing for delivering a medical image and imaging conditions is then terminated.

According to the medical image service system of the third embodiment, since imaging conditions are sent by the medical image central management server apparatus 200 to the delivery destination of the medical image (which may be either the hospital that took the medical image or another hospital) via the network 1, imaging under the same imaging conditions as in the past can be performed without need for resetting.

FOURTH EMBODIMENT

FIG. 10 is a block diagram showing a medical software service system 4000 in accordance with a fourth embodiment.

The medical software service system 4000 comprises a network 1 such as the Internet, a LAN or WAN, an A-hospital 21, B-hospital 22, C-hospital 23, D-hospital 24, and a vendor 60 that develops medical software, and a medical software central management server apparatus 400, all connected to the network 1.

The medical software central management server apparatus 400 comprises a communication section 10A, an input section 10B, an output section 10C, a security management section 10D, a medical software database management section 10H and a medical software database 401, and operates under the control of medical software central management program.

When the network 1 is the Internet, a non-subscriber 50 is also connected to the network 1. The non-subscriber 50 is a terminal that has not concluded a contract to use the medical software central management server apparatus 400.

In addition, it is preferred to use an SSL or the like in the interest of security.

Each of the A-hospital 21, B-hospital 22, C-hospital 23 and D-hospital 24 has entered into a contract to register as a software-executing subscriber permitted to run medical software (for example, an application program defining a scan algorithm) registered in the database in the medical software central management server apparatus 400. It acts as a software-executing subscriber by running on its terminal a software-executing subscriber program. This program is recorded on a storage medium (such as a CD-ROM, FD) and delivered by a manager of the medical software central management server apparatus 400, or is delivered via the network 1. Thus, the A-hospital 21, B-hospital 22, C-hospital 23 and D-hospital 24 are permitted to read medical software via the network 1 and run the medical software.

Figure 11:
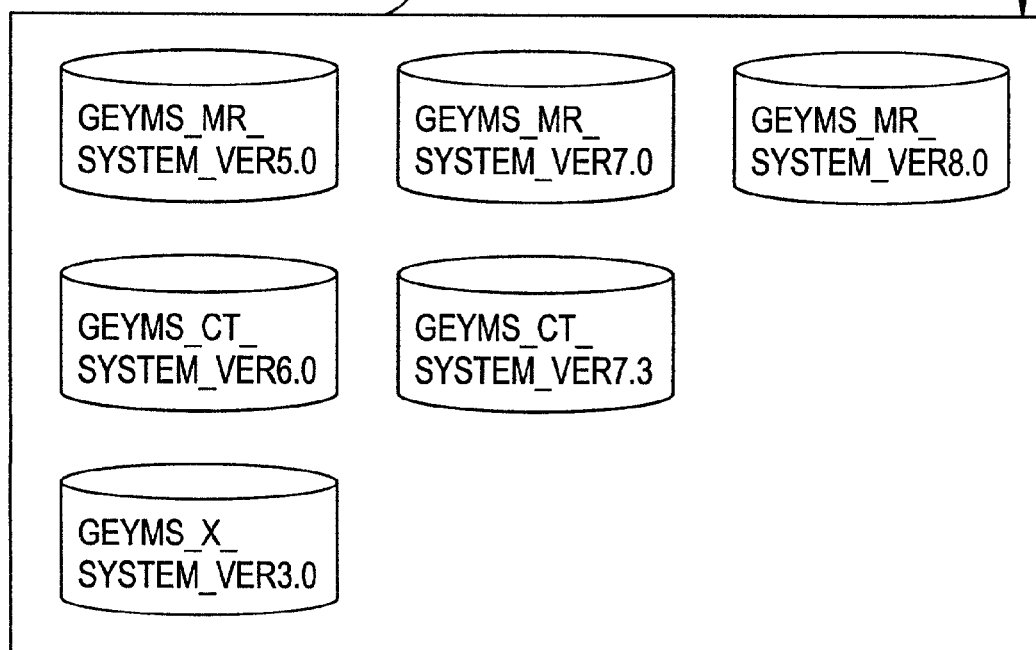
FIG. 11 is an exemplary diagram showing the registered contents in a medical software database.

FIG. 11 is an exemplary diagram showing the registered contents of the medical software database 401.

In the column designated "Installation Site", A-hospital, B-hospital, C-hospital . . . are registered, for example, as the installation sites of medical image diagnosis apparatuses that use medical software.

In the column designated "Update Date", 3-23-2000 3:35, 3-23-2000 1:47, 3-28-2000 3:21, . . . are registered, for example, as the latest dates of updates for medical software.

In the column designated "Apparatus ID", A_MRI#2, A_MRI#1, A_CT#1, . . . are registered, for example, as the apparatus IDs of medical image diagnosis apparatuses.

In the column designated "Medical Software ID", IDs pointing to medical software stored in the medical software storage section 401S, for example, GEYMS_MR_SYSTEM_VER5.0, GEYMS_CT_SYSTEM_VER7.3, . . . are registered.

The operation of the medical software service system 4000 of FIG. 10 will now be described.

When the vendor 60 has developed new medical software or upgraded existing medical software, it registers the medical software in the medical software database 401 in the medical software central management server apparatus 400 via the network 1. Specifically, the object medical software is stored in the medical software storage section 401S and the contents in the columns of FIG. 11 are newly registered or updated. It should be noted that the security management section 10D in the medical software central management server apparatus 400 comprises the function of preventing illegitimate registration by the non-subscriber 50.

In performing imaging by a medical image diagnosis apparatus, the A-hospital 21, B-hospital 22, C-hospital 23 and D-hospital 24 access the medical software central management server apparatus 400 via the network 1, read out medical software registered on the medical software database 401, and run the medical software. It should be noted that the security management section 10D in the medical software central management server apparatus 400 comprises the function of preventing illegitimate running of the software by the non-subscriber 50.

According to the medical software service system 4000 of the fourth embodiment, since the medical image diagnosis apparatus in each hospital reads out medical software registered on the medical software database 401 in the medical software central management server apparatus 400 via the network 1 and runs the medical software, immediate utilization of the latest medical software is possible at all times without need for troublesome work.

It should be noted that instead of directly running medical software stored in the medical software storage section 401S on a medical image diagnosis apparatus in a hospital, the medical software may be first installed in a local storage device and run.

Moreover, the medical software may be run in the medical software central management server apparatus 400 and the result may be delivered to a medical image diagnosis apparatus.

Furthermore, the medical software may be a product version that has been formally released, or may be a sample version released for trial. (By running the sample version, an evaluation can be made as to whether the software should be formally introduced.)

FIFTH EMBODIMENT

Figure 12:
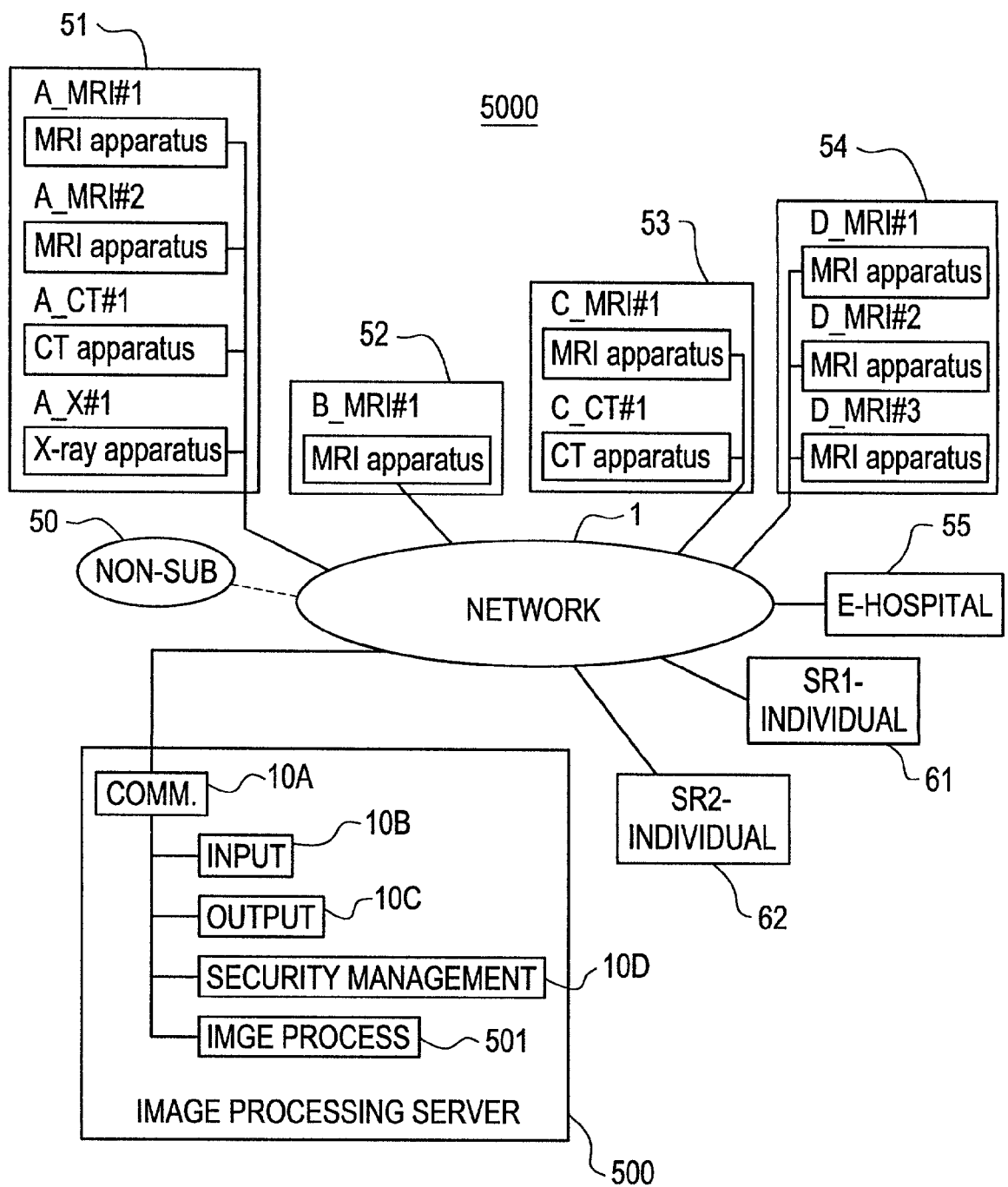
FIG. 12 is a block diagram showing a medical image service system in accordance with a fifth embodiment.

FIG. 12 is a block diagram showing a medical image service system 5000 in accordance with a fifth embodiment of the present invention.

The medical image service system 5000 comprises a network 1, an A-hospital 51, B-hospital 52, C-hospital 53, D-hospital 54, E-hospital 55, and an SR1-individual 61 and SR2-individual 62, and an image processing server apparatus 500, all connected to the network 1.

When the network 1 is the Internet, a non-subscriber 50 is also connected to the network 1. The non-subscriber 50 is a terminal that has not concluded a contract to use the image processing server apparatus 500.

In addition, it is preferred to use an SSL or the like in the interest of security.

In the A-hospital 51, MRI apparatuses (A_MRI#1, A_MRI#2), a CT apparatus (A_CT#1) and an X-ray imaging apparatus (A_X#1) are installed.

In the B-hospital 52, an MRI apparatus (B_MRI#1) is installed.

In the C-hospital 53, an MRI apparatus (C_MRI#1) and a CT apparatus (C_CT#1) are installed.

In the D-hospital 54, MRI apparatuses (D_MRI#1, D_MRI#2, D_MRI#3) are installed.

Moreover, at least one of ultrasound diagnosis, PET and CR apparatuses may be installed instead of, or in addition to, the aforementioned apparatuses in any hospital.

The image processing server apparatus 500 comprises a communication section 10A, an input section 10B, an output section 10C, a security management section 10D and an image processing section 501, and operates under the control of an image processing program.

The A-hospital 51 and B-hospital 52 have entered into contracts to register as image-sending/receiving subscribers permitted to send/receive medical images. They act as image-sending/receiving subscribers by running on their terminals an image-sending/receiving subscriber program. This program is recorded on a storage medium (such as a CD-ROM, FD) and delivered by a manager of the image processing server apparatus 500, or is delivered via the network 1. Thus, the A-hospital 51 and B-hospital 52 are permitted to send and receive medical images via the network 1.

The C-hospital 53 has entered into a contract to register as an image-sending subscriber of the image processing server apparatus 500. It acts as an image-sending subscriber by running on its terminals an image-sending subscriber program. This program is recorded on a storage medium and delivered by the manager of the image processing server apparatus 500, or is delivered via the network 1. Thus, the C-hospital 53 is permitted to send medical images via the network 1.

The D-hospital 54, E-hospital 55, SR1-individual 61 and SR2-individual 62 have entered into contracts to register as image-receiving subscribers of the image processing server apparatus 500. They act as image-receiving subscribers by running on their terminals an image-receiving subscriber program. This program is recorded on a storage medium and delivered by the manager of the image processing server apparatus 500, or is delivered via the network 1. Thus, the D-hospital 54, E-hospital 55, SR1-individual 61 and SR2-individual 62 are permitted to receive medical images via the network 1.

The manager of the image processing server apparatus 500 concludes separate contracts with the individual image-sending subscribers and image-receiving subscribers, by which the image-sending subscribers (including image-sending/receiving subscribers) are permitted to apply image processing to medical images they send, and the medical images subjected the image processing are sent to the image-receiving subscribers (including the image-sending/receiving subscribers). As a result of these contracts, the subscribers do not (have no need to) conclude contracts with one another. The image processing server apparatus 500 applies image processing to medical images sent by the image-sending subscribers and sends the medical images subjected to the image processing to the image-receiving subscribers via the network 1. The image processing server apparatus 500 also performs security management. The image processing is, for example, image filtering processing such as smoothing, differentiation, Laplacian, edge detection and band pass, or projection processing such as addition, subtraction and MIP (maximum intensity projection).

Moreover, the manager receives any one of a fixed fee, a volume fee or a combination thereof from each subscriber. For example, the manager receives a subscription fee upon making a contract. Moreover, the manager also receives a management fee regularly or irregularly for services such as maintenance and update of the subscriber information. Furthermore, the manager markets the aforementioned programs. In addition, the manager receives a fee from the subscriber that is proportional to the volume of the medical images (the number of medical images or the data size etc.) subjected to image processing or the number of image processing sessions or the image processing time.

Figure 13:
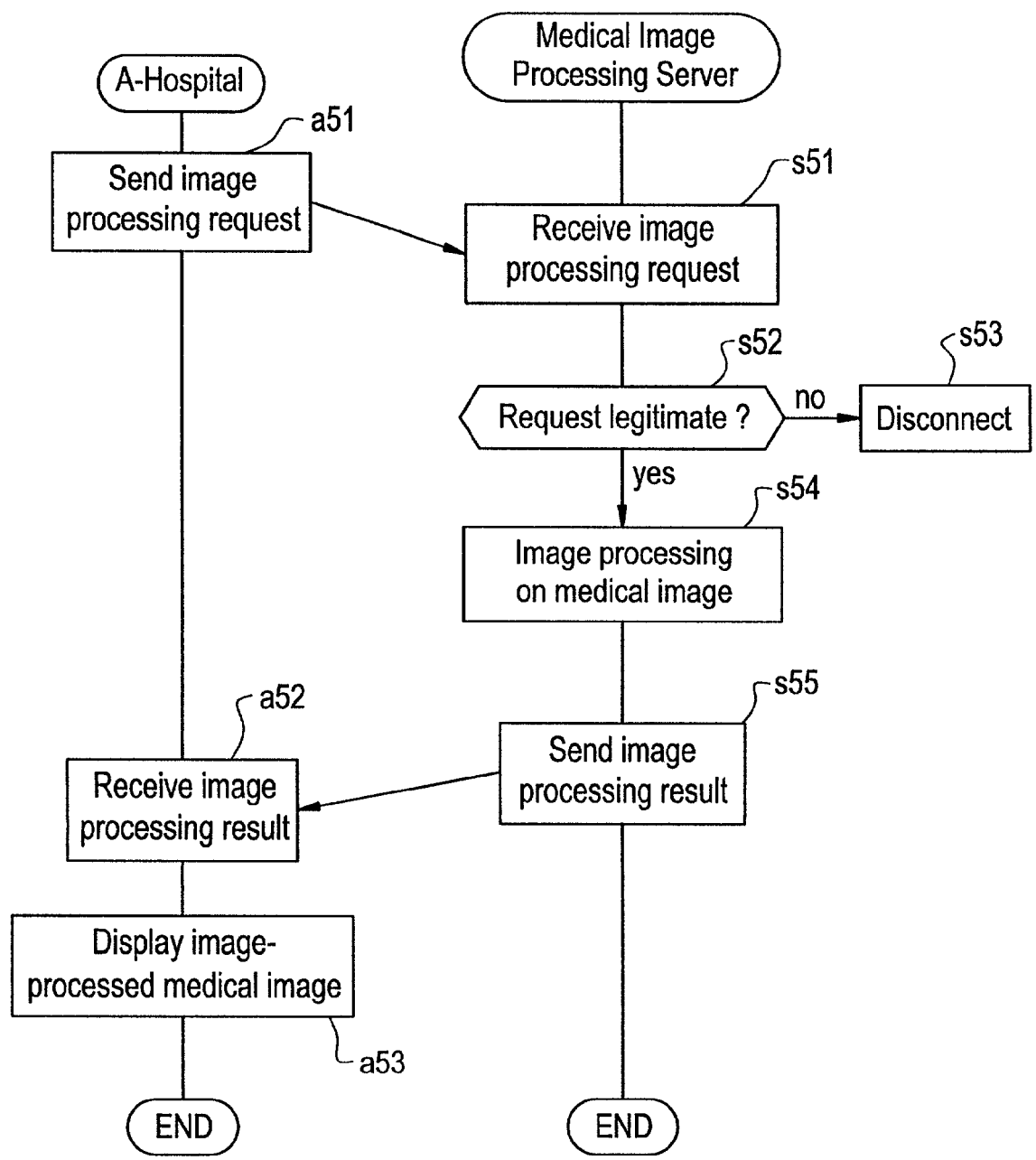
FIG. 13 is a flow chart showing processing for applying image processing to a medical image and sending the processed image back to an image-sending/receiving subscriber by an image processing server apparatus.

FIG. 13 is a flow chart showing processing for sending a medical image to the medical image server apparatus 500 and receiving the medical image subjected to the image processing, by an image-sending/receiving subscriber. The flow on the left is for the image-sending/receiving subscriber (assuming the image-sending/receiving subscriber to be the A-hospital 51). The flow on the right is for the image processing server apparatus 500.

Figure 14:
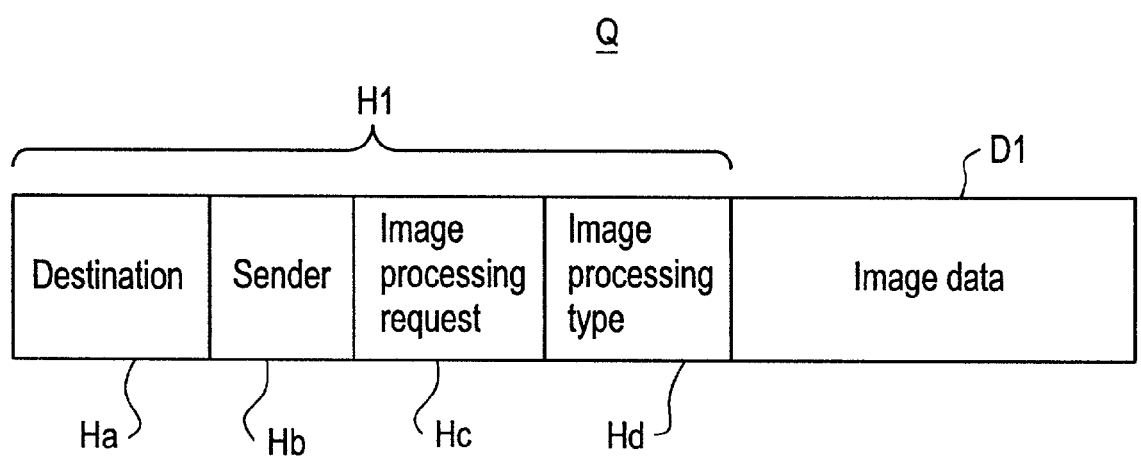
FIG. 14 is a diagram illustrating the data structure of an image processing request.

In Step a51, the A-hospital 51 (any one of the MRI, CT or X-ray imaging apparatuses) sends an image processing request Q containing image data of a medical image (any one of MRI, CT or X-ray images) to the image processing server apparatus 500 via the network 1. As shown in FIG. 14, the image processing request Q consists of a header portion H1 (a destination Ha, a sender Hb, an image processing request command Hc and an image processing type Hd) and image data D1. In this example, the destination Ha is the address of the image processing server apparatus 500. The sender Hb is the address of the A-hospital 51. The image processing request command Hc and the image processing type Hd are bit sequences for requesting, for example, MIP processing. The image data D1 is that, for example, of an MRI image.

In Step s51, the image processing server apparatus 500 receives the image processing request Q.

In Step s52, the security management section 10D in the image processing server apparatus 500 checks the legitimacy of the medical image processing request using an authentication technique etc., and if it is illegitimate, the process goes to Step s53; otherwise to Step s54.

In Step s53, the communication line is disconnected.

In Step s54, the image processing server apparatus 500 extracts the image data D1 (see FIG. 14) from the image processing request Q. Then, the image processing specified in the image processing type Hd is applied to the image data D1 by the image processing section 501.

Figure 15:
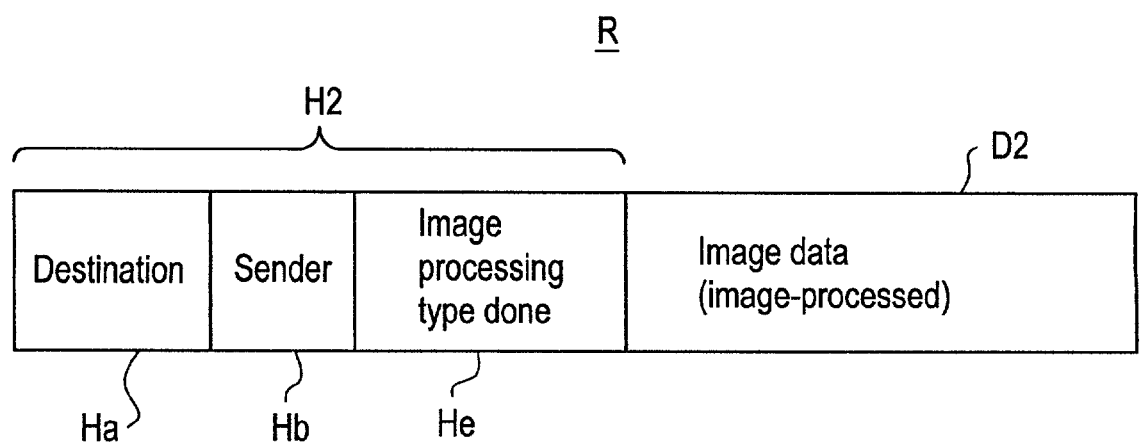
FIG. 15 is a diagram illustrating the data structure of an image processing result.

In Step s55, the image processing server apparatus 500 informs the A-hospital 51 of the image processing result R via the network 1. As shown in FIG. 15, the image processing result R consists of a header portion H2 (a destination Ha, a sender Hb and an image processing type done He) and image data D2 subjected to the image processing. In this example, the destination Ha is the address of the A-hospital 51. The sender Hb is the address of the image processing server apparatus 500. The image processing type done He is a bit sequence representing the MIP processing. The image data D2 is that subjected to the MIP processing.

In Step a52, the A-hospital 51 receives the image processing result R.

In Step a53, the A-hospital 51 extracts the image data D2 from the image processing result R, and displays the medical image subjected to the image processing (in this example, an MRI image subjected to the MIP processing).

According to the medical image service system 5000 of the fifth embodiment, the image-sending/receiving subscriber (the A-hospital 51 or B-hospital 52) sends a medical image to the image processing server apparatus 500 via the network 1, and receives the medical image subjected to image processing from the image processing server apparatus 500 and displays the medical image. Therefore, during the processing for imaging by a medical image diagnosis apparatus, the apparatus can receive and display a medical image subjected to image processing without sacrificing the processing speed of imaging.

Moreover, since the need for installing an image processing program on a medical image diagnosis apparatus is eliminated, the image-sending/receiving subscriber can easily obtain a medical image subjected to image processing. Thus, for example, a customer having a specific image processing program (which may be one purchased from the vendor of the image processing section 501 or from another vendor) installed on a medical image diagnosis apparatus can easily try or use other image processing.

Although in the fifth embodiment the medical image subjected to image processing is sent back to the image-sending/receiving subscriber that was the sender, the medical image subjected to image processing can instead be sent to an image-receiving subscriber other than the sender. For example, the image processing server apparatus 500 may apply image processing on a medical image sent by an image-sending subscriber (for example, the C-hospital 53), and send the result to an image-receiving subscriber (any one or all of the D-hospital 54, E-hospital 55, SR1-individual 61 and SR2-individual 62). However, in this case, a delivery destination must be included in the header portion H1 of the image processing request Q (see FIG. 14).

Moreover, the image processing server apparatus 500 may temporarily disconnect the communication line upon receiving the image processing request Q, establish communication with the image-sending/receiving subscriber or image-receiving subscriber after the image processing has been completed, and then send the medical image subjected to image processing. Alternatively, after the disconnection, the image-sending/receiving subscriber or image-receiving subscriber may send a request for the medical image subjected to image processing to the image processing server apparatus 500 and receive the medical image. In these cases, the use time of the network 1 can be decreased to reduce communication costs.

SIXTH EMBODIMENT

Figure 16:
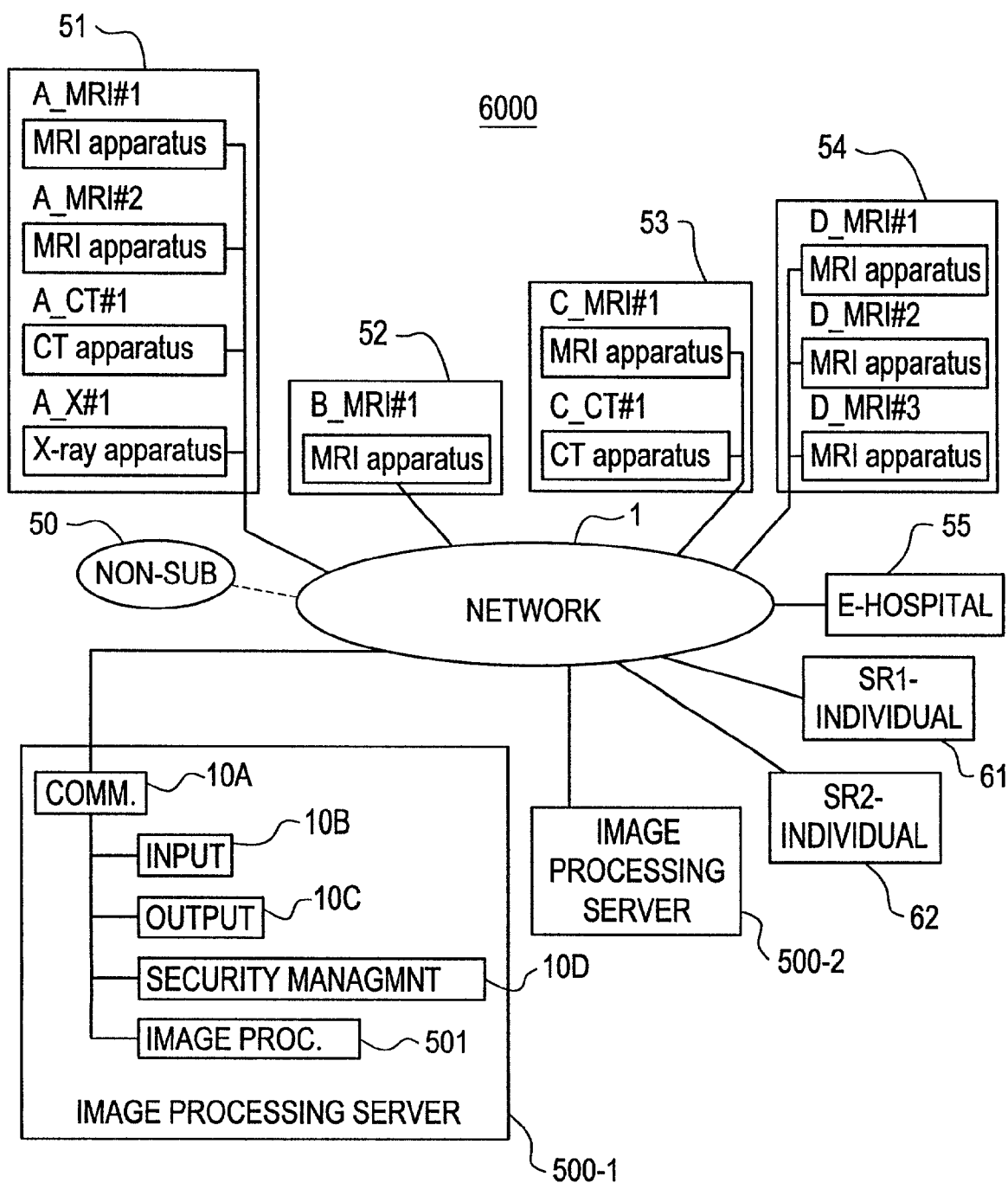
FIG. 16 is a block diagram showing a medical image service system in accordance with a sixth embodiment of the present invention.

FIG. 16 is a block diagram showing a medical image service system 6000 in accordance with a sixth embodiment of the present invention.

The medical image service system 6000 comprises image processing server apparatuses 500-1 and 500-2. The configuration of the image processing server apparatuses 500-1 and 500-2 are the same as the image processing server apparatus 500 (see FIG. 12) in accordance with the fifth embodiment.

In the medical image service system 6000, image processing on medical images is shared between the image processing server apparatuses 500-1 and 500-2. For example, when image processing is performed on 200 medical images, the image processing on the first—100$^{th}$ images is performed by the image processing server apparatus 500-1, and the image processing on the 101$^{st}$–200$^{th}$ images is performed by the image processing server apparatus 500-2. The share of the processing may be decided by the sender (an image-sending/receiving subscriber or image-sending subscriber), or may be decided by the image processing server apparatus 500-1 or 500-2 which receives the image processing request Q depending on the load status or the like.

According to the medical image service system 6000 of the sixth embodiment, the processing efficiency can be improved by sharing the load between the image processing server apparatuses 500-1 and 500-2.

SEVENTH EMBODIMENT

Figure 17:
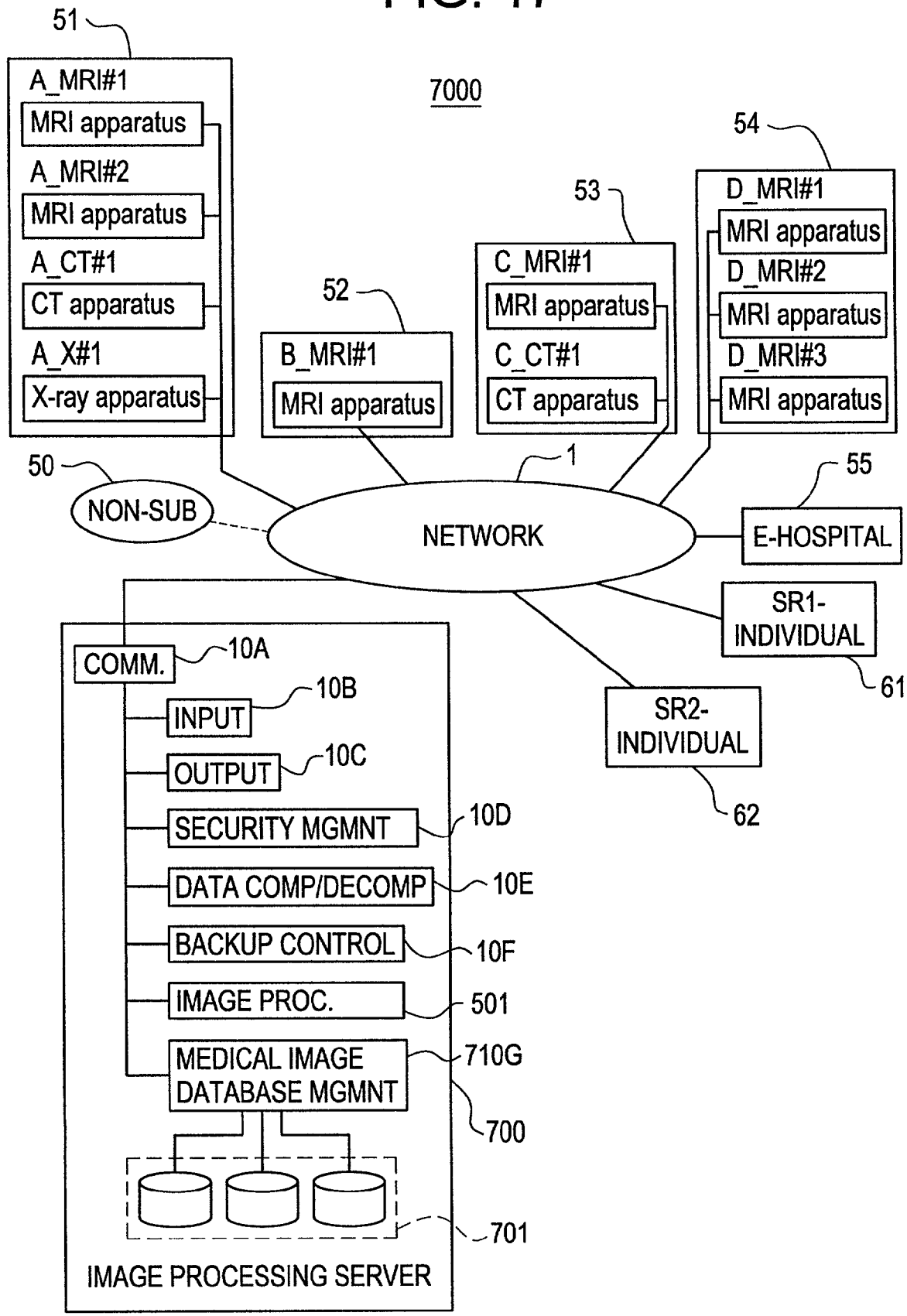
FIG. 17 is a block diagram showing a medical image service system in accordance with a seventh embodiment.

FIG. 17 is a block diagram showing a medical image service system 7000 in accordance with a seventh embodiment of the present invention.

In the medical image service system 7000, an image processing server apparatus 700 comprises a communication section 10A, an input section 10B, an output section 10C, a security management section 10D, a data compression/decompression section 10E, a backup control section 10F, an image processing section 501, a medical image database management section 701G and a medical image database 701, and operates under the control of an image processing program and a medical image central management program.

In the medical image service system 7000, medical images sent by an image-sending/receiving subscriber or image-sending subscriber are registered in the medical image database 701 in the image processing server apparatus 700 by database registration processing similar to that in the medical image service system 1000 in accordance with the first embodiment (see FIG. 2).

FIG. 18 is a flow chart showing the processing when an image-sending/receiving subscriber or image-sending subscriber makes a request to the image processing server apparatus 700 for image processing on a medical image registered in the medical image database 701 and receipt of the medical image subjected to the image processing. The flow on the left is for the image-sending/receiving subscriber (assuming the image-sending/receiving subscriber to be the A-hospital 51). The flow on the right is for the image processing server apparatus 700.

In Step a71, the A-hospital 51 sends an image processing request to the image processing server apparatus 700 via the network 1. However, it should be noted that no image data D1 (see FIG. 14) is contained in the image processing request.

In Step s71, the image processing server apparatus 700 receives the image processing request.

In Step s72, the security management section 10D in the image processing server apparatus 700 checks the legitimacy of the image processing request, and if the request is illegitimate, the process goes to Step s73; otherwise to Step s74.

In Step s73, the communication line is disconnected.

In Step s74, the image processing server apparatus 700 sends to the A-hospital 51 via the network 1 an image identifier information request for requesting image identifier information for identifying the medical image to be subjected to image processing.

In Step a72, the A-hospital 51 receives the image identifier information request.

In Step a73, the A-hospital 51 sends image identifier information to the image processing server apparatus 700 via the network 1. For example, similarly to the case described earlier with reference FIG. 5, there is sent image identifier information of an image selected from images displayed as thumbnails on the terminal in the A-hospital.

In Step s75, the image processing server apparatus 700 receives the image identifier information.

In Step s76, the medical image database management section 710G in the image processing server apparatus 700 reads the medical image corresponding to the image identifier information from the medical image database 701.

In Step s77, the image processing server apparatus 700 applies to the medical image the image processing specified by the image processing type Hd (see FIG. 14) in the image processing request.

In Step s78, the image processing server apparatus 700 sends the image processing result R (see FIG. 15) to the A-hospital 51 via the network 1. The data compression/ decompression section 10E may send data obtained by compressing the data size by a reversible method of compression.

In Step a74, the A-hospital 51 receives the image processing result. If the medical image is compressed data, the data is decompressed into the original data at the data compression/decompression section 10E.

In Step a75, the A-hospital extracts image data D2 from the image processing result R, and displays the medical image subjected to the image processing.

According to the medical image service system 7000 of the seventh embodiment, since an image-sending/receiving subscriber or image-receiving subscriber requests image processing on a medical image registered in the medical image database 701 in the image processing server apparatus 700 and receives the medical image subjected to the image processing, the need for sending the original medical image each time image processing is to be performed is eliminated, thereby reducing the processing time.

Although an original medical image is registered in the medical image database 701 in the image processing server apparatus 700 in the seventh embodiment, a medical image subjected to image processing may be registered instead of, or in addition to, the original medical image. In this case, the image processing server apparatus 700 does not need to perform image processing upon receiving an image processing request, and therefore the image processing result R can be sent more quickly. The registry region for medical images may be provided in a storage device managed by a computer other than the image processing server apparatus 700.

Moreover, the image processing server apparatus 700 may poll the image-sending/receiving subscribers or image-sending subscribers via the network 1 to collect medical images which may be requested for image processing, and register the medical images in the medical image database 701. In this case, the work of the image-sending/receiving subscribers or image-sending subscribers for sending medical images for registration can be reduced.

Many widely different embodiments of the invention may be configured without departing from the spirit and the scope of the present invention. It should be understood that the present invention is not limited to the specific embodiments described in the specification, except as defined in the appended claims.

What is claimed is:

1. A medical image servicing system comprising:
a network generally available to the public;
a plurality of subscribers having imaging devices for producing medical images and connected to said network for transmitting through said network said produced medical images for storage and for receiving through said network said stored medical images;
wherein each of said plurality of subscribers has a registration contract and/or access contract whereby the registration contract entitles the holder thereof to transmit through said network said medical images produced by imaging devices of the subscriber to a single server for storage, and whereby the access contract entitles the holder thereof to receive through said network said medical images stored in said single server;
wherein said medical images are associated with at least one image selected from the group of imaging devices producing MRI, X-ray CT, Ultrasound, PET, digitalized X-ray and CR; and
said single server, being separate from and used commonly by said plurality of subscribers, and being connected to said network for servicing said plurality of subscribers upon signaling from said plurality of subscribers; said single server comprising:
a data base for storage of said medical images produced by said imaging devices of said plurality of subscribers and transmitted through said network upon signaling by said plurality of subscribers;
means for checking and verifying legitimacy of said plurality of subscribers seeking to store said medical image in said data base of said single server or seeking to access said medical images stored in said data base of said single server;
means for registering in said data base said medical images produced by said imaging devices of said plurality of subscriber and transmitted through said network by ones of said plurality of subscribers having a registration contract upon signaling by said ones of said plurality of subscribers and upon checking and verifying legitimacy;
means for accessing in said data base said medical images registered therein by ones of said plurality of subscribers having an access contract upon signaling by said ones of said plurality of subscribers and upon checking and verifying legitimacy;
wherein said storing being equivalent to said registering of medical images in said data base;
means for compressing in data size said medical images when transmitted through said network and for decompressing in data size said medical images to original data size when received through said network by a subscriber seeking access; and
means for producing a backup of medical images registered in said data base.

2. The system of claim 1, wherein said plurality of subscribers comprise a hard copy device; and wherein at least one subscriber transmits format information including image identifier information to said hard copy device and through said network to said single server; and wherein said hard copy device receives from said single server through said network delivery of said medical images corresponding to said image identifier information and then provides a hard copy of said medical images.

3. The system of claim 1, wherein said plurality of subscribers comprise a software executing subscriber running medical software for transmission through said network to said single server; and wherein said single server manages medical software and registers said medical software transmitted through said network by at least one subscriber in said data base and causes delivery of said medical software through said network to said software executing subscriber.

4. The system of claim 1, wherein said plurality of subscribers comprise two or more subscribers, e ach connected to said network.

5. The system of claim 1, wherein said plurality of subscribers comprise means for specifying type of image processing to be communicated through said network to said single server.

6. The system of claim 1, wherein said single server comprises means for informing at least one subscriber through said network of type of image processing to be applied.

7. The system of claim 1, wherein said single server comprises means for establishing communication through said network with at least one subscriber when image processing is completed; and means for transmitting through said network said medical images subjected to said image processing to said at least one subscriber.

8. The system of claim 1, wherein said plurality of subscribers comprise means for transmitting through said network to said single server, a request for medical images subjected to image processing; and means for receiving said medical images from said single server through said network.

9. The system of claim 8, wherein said request is for only part or all of said medical images and wherein said part of all of said medical images are sent through said network to said plurality of subscribers.

10. The system of claim 1, wherein said single server comprises means for storing each medical image in at least one form before image processing; and means for storing each medical image in at least one form after said image processing.

11. The system of claim 1, wherein said single server comprises means for polling said plurality of subscribers through said network to collect medical images before image processing.

12. The system of claim 1, wherein said single server comprises means for sending through said network to a delivery destination imaging conditions for said medical images.

13. A medical image servicing method utilizing a network generally available to the public, the method comprising:
   a plurality of subscribers connected to the network and a single server connected to the network for commonly servicing the plurality of subscribers upon signaling,
   wherein each of said plurality of subscribers has a registration contract entitling that subscriber to transmit medical images produced by an imaging device located in that subscriber through the network for registering in the single server and/or an access contract entitling that subscriber to receive medical images registered in said single server and transmitted through said network to that subscriber; said method further comprising the steps of:
   a subscriber having a registration contract signaling said single server through said network to transmit medical images produced by an imaging device of said subscriber through said network to be registered by said single server after said single server checks and verifies legitimacy of the request for registration of the medical images by that subscriber;
   a subscriber having an access contract signaling said single server through said network to transmit medical images registered in said single server through network to be received by said subscriber after said single server checks and verifies legitimacy of the request for access of the medical images by that subscriber;
   compressing and decompressing data size of the medical images by the single server for registration and accessing; and
   providing back-up for the medical images in the single server.

14. The method of claim 13, wherein one subscriber requests delivery of said medical images; and comprises the further steps of:
   requesting identifier information by said single server through said network from said one subscriber;
   sending identifier information by said one subscriber to said single server through said network;
   reading medical images from said data base in said single server;
   sending each medical image from said single server through said network to said one subscriber; and
   displaying said medical images by said one subscriber.

15. The method of claim 13, wherein one subscriber requests through said network of said single server registration of said medical images; and comprises the further steps of:
   requesting imaging conditions by said single server to said one subscriber or by said one subscriber to said single server through said network;
   sending said imaging conditions by said one subscriber to said single server through said network or by said single server to said subscriber through said network; and
   said single server registering said medical images according to imaging conditions in said data base.

16. The method of claim 13, wherein one subscriber requests of said single server by signaling through said network processing of said medical images, and comprising the further steps of:
   said single server processing said medical images;
   said single server then sending results of processing through said network to said one subscriber; and
   causing said one subscriber to display results of said processing of said medical images.

17. The method of claim 16, wherein said single server further sends through said network to said one subscriber request for identification information, and said one subscriber sends such identification information to said single server through said network; wherein said single server reads medical images from said data base and processes said medical images prior to sending results thereof to said one subscriber through said network.

* * * * *